(12) United States Patent
Mendlein et al.

(10) Patent No.: US 6,585,649 B1
(45) Date of Patent: Jul. 1, 2003

(54) METHODS AND DEVICES FOR IMPROVING ULTRASONIC MEASUREMENTS USING MULTIPLE ANGLE INTERROGATION

(76) Inventors: John D. Mendlein, 680 Neptune Ave., Encinitas, CA (US) 92024; Philipp Lang, 225 Lincoln Way #206, San Francsico, CA (US) 94122

( * ) Notice: Subject to any disclaimer, the term of this patent is extended or adjusted under 35 U.S.C. 154(b) by 0 days.

(21) Appl. No.: 09/071,854

(22) Filed: May 2, 1998

(51) Int. Cl.[7] ................................................. A61B 8/00
(52) U.S. Cl. ...................................... 600/438; 600/442
(58) Field of Search ................................ 600/437, 438, 600/442, 443, 448–449; 73/597, 599

(56) References Cited

U.S. PATENT DOCUMENTS

| | | |
|---|---|---|
| 3,648,685 A | 3/1972 | Hepp et al. |
| 3,713,329 A | 1/1973 | Munger |
| 3,782,177 A | 1/1974 | Hoop |
| 3,847,141 A | 11/1974 | Hoop |
| 4,043,181 A | 8/1977 | Nigam |
| 4,048,986 A | 9/1977 | Ott |
| 4,056,970 A | 11/1977 | Sollish |
| 4,217,912 A | 8/1980 | Hubmann et al. |
| 4,224,829 A | 9/1980 | Kawabuchi et al. |
| 4,235,243 A | 11/1980 | Saha |
| 4,242,911 A | 1/1981 | Martin |
| 4,328,707 A * | 5/1982 | Clement et al. ............ 600/448 |
| 4,361,154 A | 11/1982 | Pratt |
| 4,383,533 A | 5/1983 | Lovelace et al. |
| 4,421,119 A | 12/1983 | Pratt |
| 4,446,737 A | 5/1984 | Hottier |
| 4,476,873 A | 10/1984 | Sorenson |
| 4,522,068 A | 6/1985 | Smith |
| 4,530,360 A | 7/1985 | Duarte |
| 4,658,827 A | 4/1987 | He et al. |
| 4,669,482 A | 6/1987 | Ophir et al. |
| 4,688,428 A | 8/1987 | Nicolas |
| 4,702,258 A | 10/1987 | Nicolas et al. |
| 4,774,959 A | 10/1988 | Palmer et al. |
| 4,830,015 A | 5/1989 | Okazaki |
| 4,913,157 A | 4/1990 | Pratt et al. |
| 4,930,511 A | 6/1990 | Rossman et al. |
| 5,042,489 A | 8/1991 | Wiener et al. |
| 5,054,490 A | 10/1991 | Rossman et al. |
| 5,099,849 A | 3/1992 | Rossman et al. |
| 5,119,820 A | 6/1992 | Rossman et al. |
| 5,218,963 A | 6/1993 | Mazess |
| 5,271,403 A | 12/1993 | Paulos |
| 5,343,863 A | 9/1994 | Wiener et al. |
| 5,349,959 A | 9/1994 | Wiener et al. |
| 5,452,722 A | 9/1995 | Langton |
| 5,483,965 A | 1/1996 | Wiener et al. |
| 5,547,459 A | 8/1996 | Kaufman et al. |
| 5,564,423 A | 10/1996 | Mele et al. |
| 5,603,325 A | 2/1997 | Mazess et al. |
| 5,649,538 A | 7/1997 | Langton |
| 5,651,363 A | 7/1997 | Kaufman et al. |
| 5,785,656 A | 7/1998 | Chiabrera et al. |
| 5,806,520 A | 9/1998 | Berger et al. |
| 5,810,732 A | 9/1998 | Hamatsu et al. |

FOREIGN PATENT DOCUMENTS

WO    WO 80/02796    6/1980

OTHER PUBLICATIONS

Agren M., et al., Calc Tiss Int, vol. 48, pp. 240–244, 1991.
Biot, M. A., J Acoust Soc Am, vol. 34, pp. 1254–1264, 1962.
Blake, G. M., et al., Br J Radiol, vol. 67, pp. 1206–1209, 1994.

(List continued on next page.)

*Primary Examiner*—Francis J. Jaworski

(57) ABSTRACT

The invention provides for ultrasonic methods, compositions and devices, particularly methods, compositions and devices that provide for interrogating with ultrasonic transducer(s) at multiple transmission angles in an anatomic region. The invention provides for improved interrogation devices that reduce tissue artifacts arising from heterogenous structures in tissues.

20 Claims, 12 Drawing Sheets

OTHER PUBLICATIONS

Brooke–Wavell, K., et al., Calc Tissue Int, vol. 57, pp. 20–24, 1995.
Chappard, C., et al., Osteoporosis Int, vol. 7, pp. 316–322, 1997.
Dretakis, E., et al., Br J Radiol, vol. 67, pp. 636–638, 1994.
Evans, W. D., et al., Phys Med Biol, vol. 40, pp. 137–151, 1995.
Faulkner, K. G., et al., Am J Roentgenol, vol. 157, pp. 1229–1237, 1991.
Fournier, B., et al., Osteoporosis Int., vol. 7, pp. 363–369, 1997.
Gluer, C. C., et al., J Bone Min Res, vol. 7 (9), pp. 1071–1079, 1992.
Gluer, C. C., et al., Calc Tiss Int, vol. 55, pp. 46–52, 1994.
Goss, S. A., et al., J. Acoust Soc Am, vol. 64 (2), pp. 423–457, 1978.
Greenspan, M., et al., J Acoust Soc Am, vol. 31, pp. 75–76, 1959.
Hans, D., et al., Bone, vol. 16, pp. 295–300, 1995.
Johansen A., et al., Osteoporosis International, vol. 7, pp. 44–47, 1997.
Laugier P., et al., Calc Tiss Int, vol. 54, pp. 83–86, 1994.
Kotzki, P. O., et al., Calc Tiss Int. vol. 54, pp. 91–95, 1994.
Lang, P., et al., Radiol Clin North Am, vol. 29, pp. 49–76, 1991.
Langton, C. M., et al.,Bone, vol. 18, 6, pp. 495–503, 1996.
Langton, C.M. et al., Eng. Med, vol. 13, pp. 89–91, 1984
Laugier, P., et al., Bone, vol. 20 (2),pp. 157–165,1997.
Laugier, P., et al., Calc Tiss Int, vol. 58, pp. 326–331, 1996.
Laugier, P., et al., Clinical Rheumatology, vol. 13 (Suppl. 1), pp. 23–32, 1994.
Laugier, P., et al. Calc Tiss Int, vol. 54, pp. 83–86, 1994.
McCloskey, E. V., et al., Clin Sci, vol. 78, pp. 83–86, 1994.
Njeh, C. F., et al., Med Eng Phys, vol. 18, pp. 373–381, 1996.
Roux, C., et al., J Bone Min Res, 11 (8), pp. 1112–1118, 1996.
Turner, C. H., et al., Calc Tiss Int, vol. 49, pp. 1991.
Williams, J. L., Acoust Soc Am, vol. 91, pp. 1106–1112, 1992.
Zagzebski, J. A., et al., Calc Tiss Int, vol. 49, pp. 107–111, 1991.

\* cited by examiner

RECEIVED SIGNALS

No Tissue

First Physiologic State

α axis of transmission

β axis of transmission

Second Physiologic State

α axis of transmission

β axis of transmission

US 6,585,649 B1

METHODS AND DEVICES FOR IMPROVING ULTRASONIC MEASUREMENTS USING MULTIPLE ANGLE INTERROGATION

TECHNICAL FIELD

The invention relates to ultrasonic methods, compositions and devices, particularly methods, compositions and devices that provide for multiple angle interrogation with ultrasonic transducer(s) over an anatomical region.

BACKGROUND

Ultrasonic techniques are often used as methods free of ionizing radiation for non-invasive assessment of anatomy, such as skeletal status in patients with osteoporosis. Quantitative aspects of these ultrasonic techniques can permit assessment of bone mass and density, as well as bone structure. Ultrasonic techniques for evaluating skeletal status also include measurements of speed of sound ("SOS") that reflect the transmission velocity of ultrasonic waves passing through bone tissue and soft tissue, measurements of broadband ultrasonic attenuation ("BUA") that assess the frequency dependence of ultrasonic attenuation, and pulse echo techniques that measure the energy scattered from the internal structure of the bone.

Many different measurement sites have been proposed for osteoporosis, such as the tibia, the patella, the phalanges, or the calcaneus. The calcaneus is preferred for quantitative ultrasonic measurements of skeletal status. It is composed of predominantly trabecular bone with only a thin cortical bone envelope medially and laterally, which together provide an excellent medium for detecting changes in SOS and BUA measurements. The calcaneus also permits convenient ultrasonic interrogation for the operator and the patient alike.

Although a number of commercial devices exist for diagnosis of osteoporosis, clinicians have recognized the limitations of such devices and methods. Correlations between quantitative ultrasonic measurements and assessments of bone mineral density using quantitative computed tomography, dual x-ray absorptiometry, and single photon absorptiometry have been reported to be poor at the calcaneus, as well as at other sites.

In addition, ultrasonic measurements of tissue, particularly in the calcaneus, often suffer from heterogenous tissue structures. Such structures as described herein can interfere with interrogation, which leads to deceased accuracy and precision of such measurements.

Consequently, the inventors have recognized the need, among other things, to provide reliable ultrasonic devices and accurate, and qualitative or quantitative methods for ultrasonic measurements in the diagnosis of osteoporosis, as well as methods and devices to generally improve diagnostic tools based on ultrasonic measurements. The methods and devices provide herein permit, among other things, correction of ultrasonic parameters, such as speed of sound and broadband ultrasonic attenuation, for soft tissue structures interposed in the ultrasonic beam and tissue heterogeneity and variations.

SUMMARY

While many of the embodiments of the invention will find particular application in clinical measurements, such as BUA or SOS, and surgical procedures, such trocar procedures and catheter procedures, the invention provides for general ultrasonic devices and methods that will be applicable to many clinical applications.

The invention includes an ultrasonic system for multiple transmission angle ultrasonic interrogation in tissues with heterogenous structures that alter ultrasonic properties. The system can comprise a first ultrasonic transducer with an axis of transmission in common with a second ultrasonic transducer, said axis of transmission is through a portion of tissue suspected of having heterogenous structures that alter ultrasonic properties. The system can include an x, y positioner that can engage the first ultrasonic transducer and the second ultrasonic transducer. The x, y positioner controllably 1) positions the first ultrasonic transducer and the second ultrasonic transducer in a desired manner between at least a first and a second position while generally maintaining the axis of transmission and 2) establishes predetermined transmission angles for the first ultrasonic transducer and the second ultrasonic transducer to interrogate the portion of the tissue at multiple transmission angles through heterogenous structures in the tissue. A computational unit can be included that is designed to manage ultrasonic signal transmission and reception of the first ultrasonic transducer and the second ultrasonic transducer with either BUA or SOS or both. It may optionally be designed to control movement of the x, y positioner. The ultrasonic measurements with multiple transmission angles are typically improved compared to interrogation in the absence of multiple transmission angles.

In addition, the invention includes an ultrasonic system for automated ultrasonic measurements at multiple transmission angles. The system comprises an ultrasonic transducer unit comprising 1) an ultrasonic transducer that can transmit and receive signals and 2) a multiple transmission angle positioner to vary the transmission angle of the ultrasonic transducer with respect to the plane of a tissue in a predetermined fashion. Preferably, the transducer unit is designed to vary the transmission angle without necessarily changing the general position of the ultrasonic transducer with respect to the tissue. This allows the substantially same region to be interrogated at different angles. The system can include a computational unit designed to manage ultrasonic signal transmission and reception of the ultrasonic transducer unit and to process signals from the ultrasonic transducer unit at multiple transmission angles, for example using signal averaging, filtering unwanted signals or pattern recognition of desired types of acoustic signatures. Preferably, the computational unit is designed to process received ultrasonic signals from the ultrasonic transducer to generate at least one data set of an ultrasonic property determined at predetermined, multiple transmission angles. Such an ultrasonic property can be selected from the group consisting of broadband ultrasonic attenuation, echogenicity, reflective surfaces, distances from the transducer unit, speed of sound, and ultrasonic images.

In addition, the invention includes an ultrasonic system for tissue ultrasonic interrogation for broadband ultrasonic attenuation at multiple transmission angles. The system comprises a first ultrasonic transducer with an axis of transmission through an anatomical region to be interrogated and the first ultrasonic transducer is adapted for BUA and a second ultrasonic transducer adapted for BUA with the axis of transmission through the anatomical region to be interrogated, wherein monitoring broadband ultrasonic attenuation between the first ultrasonic transducer and the second ultrasonic transducer is permitted. The system includes a positioning unit to vary the transmission angle of the axis of transmission with respect to the tissue plane. The system may have a computational unit designed to manage ultrasonic signal transmission of the first ultrasonic transducer, to manage ultrasonic signal reception of the second ultrasonic transducer and to control the transmission angle of the axis of transmission. Typically, the positioning unit comprises an x,y positioner for the first ultrasonic transducer and the second ultrasonic transducer that can establish at least 3 predetermined transmission angles while maintaining a common axis of transmission. Preferably, the x,y positioner is designed to position the first ultrasonic transducer and the second ultrasonic transducer with first axis of transmission at each transmission angle generally passing through the same anatomical region. Typically, the center of axis of transmission at each angle passes through an area of the anatomical region that is no more than about 5 to 8 cm squared.

The invention also includes an ultrasonic method for ultrasonic interrogation at multiple transmission angles. The method comprises positioning, with respect to an anatomical region, an ultrasonic transducer unit comprising either 1) a first ultrasonic transducer that can transmit and receive signals or 2) a pair of ultrasonic transducers where a first member of the pair is designed to transmit signals and a second member of the pair is designed to receive signals. The methods includes interrogating the anatomical region with the ultrasonic transducer unit at predetermined, multiple transmission angles, and recording an ultrasonic property of the anatomical region. The method further comprises storing the ultrasonic property in a storage device.

The invention also includes an ultrasonic method for determining broadband ultrasonic attenuation or speed of sound measurements in dense tissues. The method comprises interrogating a tissue at predetermined, multiple transmission angles with an ultrasonic transducer unit adapted for either 1) broadband ultrasonic attenuation or 2) speed of sound measurements or both. The method includes determining dense tissue broadband ultrasonic attenuation, dense tissue speed of sound or both at two or more predetermined, multiple transmission angles, wherein the determining step generates a dense tissue broadband ultrasonic attenuation value, dense tissue speed of sound value or both that is more indicative of broadband ultrasonic attenuation or speed of sound in dense tissue than interrogation in the absence of predetermined, multiple transmission angles.

The invention also includes an ultrasonic method for generating an anatomic landmark for ultrasonic interrogation of an anatomical region, comprising:

positioning, if necessary, on the surface of a patient, with respect to an anatomical region, an ultrasonic transducer unit comprising either 1) a first ultrasonic transducer that can transmit and receive signals or 2) a pair of ultrasonic transducers wherein a first member of the pair is designed to transmit signals and a second member of the pair is designed to receive signals, and interrogating the anatomical region with the ultrasonic transducer unit at a first transmission angle, interrogating the anatomical region with the ultrasonic transducer unit at a second transmission angle, identifying an anatomic landmark in common with the signals obtained in the above steps in the anatomical region with an ultrasonic property of the anatomical region.

The invention also includes an ultrasonic method for determining broadband ultrasonic attenuation or speed of sound measurements in dense tissues, comprising:

interrogating a patient's tissue with at least a first ultrasonic transducer unit at a first transmission angle and a second ultrasonic transducer unit at a second transmission angle, wherein said first ultrasonic transducer unit and said second ultrasonic transducer unit are a) adapted for either 1) broadband ultrasonic attenuation or 2) speed of sound measurements or both and b) have an angle of least about 150 degrees between said first ultrasonic transducer unit and said second transducer unit, interrogating said patient's tissue with said first ultrasonic transducer unit at a third transmission angle and said second ultrasonic transducer unit at a fourth transmission angle while maintaining an angle of at least about 150 degrees between said first transducer unit and said second transducer unit, and determining dense tissue broadband ultrasonic attenuation, dense tissue speed of sound or both for said tissue; wherein said determining step generates a dense tissue broadband ultrasonic attenuation value, dense tissue speed of sound value or both that is more indicative of broadband ultrasonic attenuation or speed of sound in dense tissue than in the absence of interrogating said patient's tissue with at least said first ultrasonic transducer unit at a third transmission angle and said second ultrasonic transducer unit at a fourth transmission angle.

The invention also includes an ultrasonic system for determining broadband ultrasonic attenuation or speed of sound measurements in a tissue, comprising:

a transducer unit comprising at least a first ultrasonic transducer engaged with a first multiple transmission angle unit to controllably vary first transmission angles and a second ultrasonic transducer engaged with a second multiple transmission angle unit to controllably vary second transmission angles, wherein the first ultrasonic transducer unit and the second ultrasonic transducer unit are adapted for either 1) broadband ultrasonic attenuation or 2) speed of sound measurements or both, and a computational unit for controllably adjusting transmission angles of the first and second transducer; wherein the ultrasonic system will measure broadband ultrasonic attenuation value, speed of sound value or both if so desired.

The invention also includes a computer program product, comprising:

instructions for a positioning unit to vary the transmission angle of a transducer or plurality of transducers at a plurality of transmission angles in an anatomical region, instructions for interrogating the anatomical region with the transducer or the plurality of transducers at the plurality of transmission angles, and instructions for recording at least one ultrasonic property at the plurality of transmission angles, wherein the above instructions facilitates a clinically relevant measurement and such instructions are stored on a computer retrievable medium.

DETAILED DESCRIPTION OF THE INVENTION

1.0 Abbreviations and Definitions

Figure 1A:
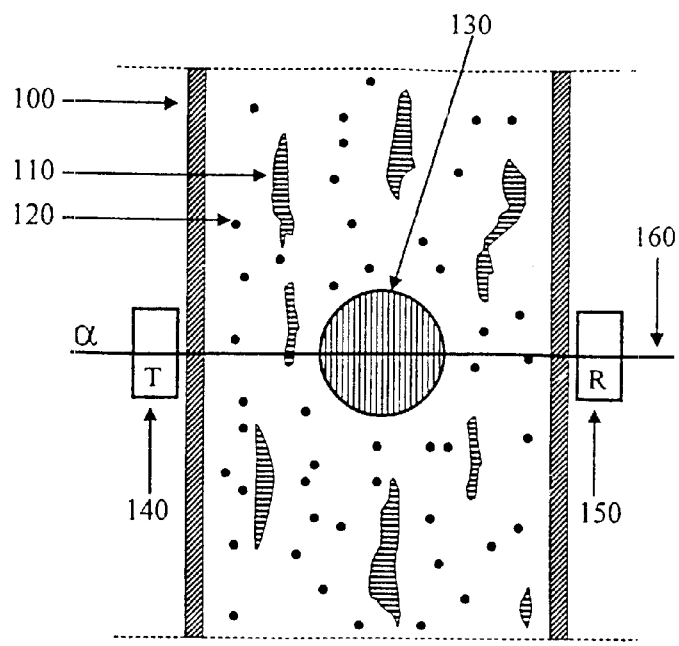
FIG. 1A and FIG. 1B show a tissue interrogated by an ultrasonic transducer (140; T) that transmits to an ultrasonic receiver (150; R) (or detector) at different transmission angles and with different axes of transmission. The axis of transmission is shown as $\alpha$ (or $\beta$) and has a transmission path from T to R.

Abbreviations include broadband ultrasonic attenuation (BUA) and speed of sound (SOS).

Acoustic communication refers to the passage of ultrasonic waves between two points in a predetermined manner. Usually, this is accomplished by selecting a desired pathway between the two points that permits the passage of ultrasonic waves either directly or indirectly. Direct passage of ultrasonic waves would occur, for instance, when an ultrasonic crystal is directly disposed to (usually touching) an acoustic coupling material, such as a composite. Indirect passage of ultrasonic waves would occur, for instance, when an ultrasonic crystal is located at a predetermined distance from an acoustic coupling material or when a number of acoustic coupling materials, often heterogenous materials, form two or more layers.

Acoustic coupler refers to a connection or plurality of connections between an ultrasonic crystal and a substance that reflects or passes ultrasonic pulses and is not part of the device or object being interrogated. The acoustic coupler will permit passage of ultrasonic waves. It is desirable for such couplers to minimize attenuation of ultrasonic pulses or signals and to minimize changes in the physical properties of an ultrasonic wave, such as wave amplitude, frequency, shape and wavelength. Typically, an ultrasonic coupler will either comprise a gel or other substantially soft material, such as a pliable polymer matrix, that can transmit ultrasonic pulses.

Acoustic coupling material is a material that passes ultrasonic waves, usually from a probe to a subject or tissue to be interrogated. It is usually not a living material and is most often a polymer or gel or acoustic coupler.

Acoustic mirror refers to a device that can reflect an ultrasonic wave and redirect the ultrasonic wave in a predetermined manner. If the original ultrasonic waves are transmitted at an angle α, which is measured relative to the surface of the plane of the acoustic mirror, the reflected ultrasonic waves can be oriented at an angle $\alpha'=180°-\alpha$ relative to the plane of the acoustic mirror. An acoustic mirror(s) can be used in an ultrasonic system to vary the transmission angle.

Anatomical region refers to a site on the surface of the skin, tumor, organ or other definable biomass that can be identified by an anatomical feature(s) or location. Anatomical region can include the biomass underlying the surface. Usually, such a region will be definable according to standard medical reference methodology, such as that found in Williams et al., Gray's Anatomy, 1980.

BUA means broadband ultrasonic attenuation and when measured a BUA value is expressed as dB/MHz. Note that actual attenuation of broadband ultrasonic waves increases as soft tissue thickness increases, while BUA values (dB/MHz) decrease as soft tissue thickness increases. This distinction is often not recognized in the literature, which leads to misleading or potentially misleading conclusions about the effect of soft tissue on actual attenuation of broadband ultrasonic waves and BUA values.

A-scan refers to an ultrasonic technique where an ultrasonic source transmits an ultrasonic wave into an object, such as a patient's body, and the amplitude of the returning echoes (signals) are recorded as a function of time. Structures that lie along the direction of propagation are interrogated. As echoes return from interfaces within the object or tissue, the transducer crystal produces a voltage that is proportional to the echo intensity. The sequence of signal acquisition and processing of A-scan data in a modern ultrasonic instrument usually occurs in six major steps:

Detection of the echo (signal) occurs via mechanical deformation of the piezoelectric crystal and is converted to an electric signal having a small voltage.

Preamplification of the electronic signal from the crystal, into a more useful range of voltages is usually necessary to ensure appropriate signal processing.

Time Gain Compensation compensates for the attenuation of the ultrasonic signal with time, which arises from travel distance. Time gain compensation may be user-adjustable and may be changed to meet the needs of the specific application. Usually, the ideal time gain compensation curve corrects the signal for the depth of the reflective boundary. Time gain compensation works by increasing the amplification factor of the signal as a function of time after the ultrasonic pulse has been emitted. Thus, reflective boundaries having equal abilities to reflect ultrasonic waves will have equal ultrasonic signals, regardless of the depth of the boundary.

Compression of the time compensated signal can be accomplished using logarithmic amplification to reduce the large dynamic range (range of smallest to largest signals) of the echo amplitudes. Small signals are made larger and large signals are made smaller. This step provides a convenient scale for display of the amplitude variations on the limited gray scale range of a monitor.

Rectification, demodulation and envelope detection of the high frequency electronic signal permits the sampling and digitization of the echo amplitude free of variations induced by the sinusoidal nature of the waveform.

Rejection level adjustment sets the threshold of signal amplitudes that are permitted to enter a data storage, processing or display system. Rejection of lower signal amplitudes reduces noise levels from scattered ultrasonic signals.

B-scan refers to an ultrasonic technique where the amplitude of the detected returning echo is recorded as a function of the transmission time, the relative location of the detector in the probe and the signal amplitude. This is often represented by the brightness of a visual element, such as a pixel, in a two-dimensional image. The position of the pixel along the y-axis represents the depth, i.e. half the time for the echo to return to the transducer (for one half of the distance traveled). The position along the x-axis represents the location of the returning echoes relative to the long axis of the transducer, i.e. the location of the pixel either in a superoinferior or mediolateral direction or a combination of both. The display of multiple adjacent scan lines creates a composite two-dimensional image that portrays the general contour of internal organs.

Chip refers to any current and future electronic hardware device that can be used in a computational unit and can be used as an aid in controlling the components of an ultrasonic unit including: 1) timing and synchronizing trigger pulses and subsequent transmission of ultrasonic waves, 2) measuring and analyzing incoming ultrasonic signals, 3) comparing data to predetermined standards and data cut-offs (e.g. electronic filtering), and 4) performing multiple other simple and complex calculations. Typically, a chip is silicon-based, micro-electronic ciruit.

Computational unit refers to any current or future hardware, software (e.g. computer program), chip or other device used for calculations or for providing instructions now developed or developed in the future. The computational unit may be used for controlling the ultrasonic generator or source, for defining or varying the firing rate and pulse repetition rate (as well as other parameters related to the ultrasonic generator or source), for measuring the reflected signal, for image reconstruction in B-scan mode and for filtering and thresholding of the ultrasonic signal. Other applications of the computational unit to the methods and devices described herein will be recognized by those skilled in the art. The computational unit may be used for any other application related to this technology that may be facilitated with use of computer software or hardware. The computational unit may comprise a computer program product with instructions to control the ultrasonic system. Such computer program products may be stored in storage devices, such as hard drives, floppy discs, electronic storage devices or any other storage device capable of reliable storage and retrieval of information (including electronic signals).

Detector refers to any structure capable of measuring an ultrasonic wave or pulse, currently known or developed in the future. Crystals containing dipoles are typically used to measure ultrasonic waves. Crystals, such as piezoelectric crystals, shift in dipole orientation in response to an applied electric current. If the applied electric current fluctuates, the crystals vibrate to cause an ultrasonic wave in a medium. Conversely, crystals vibrate in response to an ultrasonic wave that mechanically deforms the crystals, which changes dipole alignment within the crystal. This, in turn, changes the charge distribution to generate an electric current across a crystal's surface. Electrodes connected to electronic circuitry sense a potential difference across the crystal in relation to the incident mechanical pressure. A transducer can be a detector.

Echogenicity refers to the brightness of a tissue in an ultrasonic image relative to the adjacent tissues, typically on a B-scan image. Echogenicity is dependent on the amount of ultrasonic waves reflected by the tissue. Certain tissues are more echogenic than other tissues. Fatty tissue, for example, is more echogenic than muscle tissue. For identical imaging parameters, fatty tissue will thus appear brighter than muscle tissue. Consequently, image brightness can be used to identify different tissues.

Frame time, when used in the context of positioning an ultrasonic source, refers to the time that is required to move an ultrasonic source from a first to a second position (or other additional positions) and back using a mechanical motor or other current and future devices. Frame time typically ranges from 10 ms to 2,000 ms.

Linear array refers to a transducer design where the crystals are arranged in a linear fashion along one or more axes. Crystals can be fired in sequential, as well as non-sequential and simultaneous firing patterns or a combination thereof. With sequential firing, each crystal can produce an ultrasonic beam and receive a returning echo for data collection. The number of crystals in one array usually determines the number of lines of sight for each recording. With segmental firing, a group or segment of crystals can be activated simultaneously resulting in a deeper near field and a less divergent far field compared with sequential activation. A segmental linear array produces, however, a smaller number of lines of sight when compared to a sequential linear array with the same number of crystals.

Mechanically connected refers to a connection between two or more mechanical components, such as an ultrasonic source having at least two transmission positions. A mechanical connection between two transmission positions may be accomplished using a mechanical motor to rotate or move an ultrasonic source. Optionally, the ultrasonic source can be rotated or moved on a track to vary the transmission angle.

Mechanical motor refers to any device that can move a device, such as the ultrasonic source, from at least a first to a second position and, if desired, to additional positions. A mechanical motor may employ a spring-like mechanism to move the ultrasonic source from the first to the second position. A mechanical motor may also employ a hydraulic, a magnetic, an electromagnetic mechanism or any other current and future mechanism that is capable of moving the ultrasonic source from a first to a second position.

Programmed mechanical motor refers to any motor controlled by a program, such as a program in a chip or computer. Such motors include mechanical, electrical or hydraulic devices to move an ultrasonic source from a first to a second position, and if desired to additional positions. The program usually defines the frame time that the mechanical motor moves the ultrasonic source from a first to a second position and back. If more than two positions are used, the program can move the ultrasonic source to many different positions, as desired.

Oscillate refers to moving the ultrasonic source repetitively from a first to a second position or other additional positions and moving it back from the second position or other additional positions. Oscillating from the first to the second position and back may be achieved using a mechanical motor. Typically, transducers will be oscillated to vary the transmission angle.

Osteoporosis refers to a condition characterized by low bone mass and microarchitectural deterioration of bone tissue, with a consequent increase of bone fragility and susceptibility to fracture. Osteoporosis presents most commonly with vertebral fractures due to the decrease in bone mineral density and deterioration of structural properties of the bone. The most severe complication is hip fracture due to its high morbidity and mortality.

Plane refers to the surface of a cross-sectional area of tissue interrogated by an ultrasonic probe. In ultrasonic measurements, the portion of the tissue included in the measurement or image is more accurately referred to as a volume. The x-dimension of this volume reflects the length of the tissue plane, i.e. the length of imaged tissue. The x-dimension typically varies between 1 and 10 cm or more. The y-dimension of this volume reflects tissue depth from the plane, e.g. the distance from the skin surface to a reflection point in the tissue. Interrogation of the y-dimension (or depth of the interrogation) depends, among other things, on the type of transducer, the type of tissue, and the frequency with which the ultrasonic beam is transmitted. With higher frequencies, tissue penetration decreases and the maximum depth from the tissue plane will decrease. The y-dimension typically varies between 1 and 30 cm. The z-dimension corresponds to the width of the plane that is interrogated. It typically varies between 1 and 15–20 mm. It is understood that such dimensions are in reference to ultrasonic signals and interrogation. In addition, x, y, and z dimensions are also used with different meaning in the context of positioning probes, and devices for locating probes in different areas of an anatomical region.

Transmission angle refers to the angle of an ultrasonic beam that intersects the object or tissue plane. The transmission angle is normally measured with respect to the object or tissue plane. The object or tissue plane has a reference angle of zero degrees. For example, as the transmission angle increases toward 90 degrees relative to the tissue plane, the ultrasonic beam approaches an orthogonal position relative to the tissue plane. Preferably, ultrasonic measurements are initiated when the ultrasonic beam is orthogonal to the plane of the tissue. Typically, the transmission angle is varied in a predetermined and controllable manner in order to interrogate anatomical region as a function of a preselected transmission angle(s). Varying the transmission angle is particularly useful for ultrasonic methods used for BUA and SOS measurements. Transmission angle can be varied by changing the position of a transducer with respect to the object to be interrogated.

First position refers to a position of an ultrasonic source (or transducer) that detects or transmits an ultrasonic signal or pulse, respectively. Typically, the first position will have a predetermined transmission angle associated with it (e.g. 90, 80, 70 or 60 degrees). BUA and SOS can also be measured at the first position and if desired compared with measurements from other positions, particularly positions that vary the transmission angle.

Second position refers to a position of an ultrasonic source (or transducer) that transmits or detects an ultrasonic pulse or signal, respectively and having either a different transmission angle from the first position or a different anatomical location than the first position. It is understood that the second position may have the same anatomical location as the first position while having a different transmission angle compared to the first position. Typically, the first position will have a predetermined transmission angle associated with it (e.g. 90, 80, 70 or 60 degrees). BUA and SOS can also be measured at the second position and if desired compared with measurements from other positions. In some applications it will be desirable for the first and second positions to generally have the same anatomical location while varying the transmission angle. Additional positions can be readily achieved by relocating the ultrasonic source to either vary the anatomical location of interrogation or the transmission angle.

Transmission frequency refers to the frequency of the ultrasonic wave that is being transmitted from the ultrasonic source. Transmission frequency typically ranges between 0.2 MHz and 25 MHz. Higher frequencies usually provide higher spatial resolution. Tissue penetration decreases with higher frequencies. Lower transmission frequencies are generally characterized by lower spatial resolution with improved tissue penetration.

Ultrasonic pulse refers to any ultrasonic wave transmitted by an ultrasonic source. Typically, the pulse will have a predetermined amplitude, frequency, and wave shape. Ultrasonic pulses may range in frequency between 20 kHz and 20 Mhz or higher. Ultrasonic pulses may consist of sine waves with single frequency or varying frequencies, as well as single amplitudes and varying amplitudes. In addition to sine waves, square waves or any other wave pattern may be employed. Square waves may be obtained by adding single-frequency sine waves to other sine waves. The summation of waves can then result in a square wave pattern.

Ultrasonic signal refers to any ultrasonic wave measured by an ultrasonic detector after it has been reflected from the interface of an object or tissue. Ultrasonic signals may range in frequency between 20 kHz and 20 Mhz or higher.

Ultrasonic source refers to any structure capable of generating an ultrasonic wave or pulse, currently known or developed in the future. Crystals containing dipoles are typically used to generate an ultrasonic wave above 20 khz. Crystals, such as piezoelectric crystals, that vibrate in response to an electric current applied to the crystal can be used as an ultrasonic source. In some ultrasonic generators, multiple ultrasonic sources may be arranged in a linear fashion. This arrangement of ultrasonic sources is also referred to as a linear array. With linear arrays, ultrasonic sources are typically fired sequentially, although simultaneous firing of groups of adjacent ultrasonic sources or other firing patterns of individual or groups of ultrasonic sources with various time delays can be achieved as described herein or developed in the art. The time delay between individual or group firings can be used to vary the depth of the beam in an object.

Ultrasonic wave refers to either an ultrasonic signal or pulse.

2.0 Introduction

The present invention recognizes for the first time that errors arising from heterogenous tissue structure in ultrasonic measurements of speed of sound and broadband ultrasonic attenuation of trabecular and cortical bone can be reduced or corrected by measuring BUA or SOS at different transmission angles. Previously, it was not recognized that ultrasonic measurements at predetermined transmission angles can be used to correct measured SOS and BUA values for errors introduced by overlying soft tissues. Nor was it recognized that tissue heterogenity is a potential source of decreased accuracy and reproducibility of SOS and BUA measurements in patients with peripheral edema undergoing diuretic or other types of medical treatment of edema with resultant fluctuations in tissue heterogeneity. The present invention includes measuring BUA and SOS using various transmission angles to reduce artifacts imposed by variations in tissue structure that can affect BUA and SOS measurements. The present invention also includes applying appropriate corrections to SOS and BUA based on ultrasonic measurements at predetermined, multiple transmission angles.

Without limiting aspects of the invention to a particular mechanism of action, the inventors believe that the poor correlations between quantitative ultrasonic techniques and other methods for assessing bone mineral density are often caused by structural variations in the interrogated tissue (including the interrogated bone) with respect to the position of the ultrasonic transducers. Sources of such interrogation artifacts include variations in the thickness of the posterior or inferior heel pads, variations in water content, variations in extracellular matrix density or content (e.g. protein), variations in soft-tissue organization, variations in cortical bone density or structure, and variations in trabecular bone density or structure. Such variations in tissue structure can affect transmission of ultrasonic waves or pulses from the transmitter to the detector in other tissues as well. Ultrasonic measurements of the tissue can also vary even if the transducer is reproducibly located at an interrogation site because ultrasonic transmission through the tissue's structure may change as a function of position or transmission angle. In all cases, differences in the tissue structures interposed in the ultrasonic beam path can ultimately change the speed of sound and broadband ultrasonic attenuation as well as other ultrasonic properties.

In addition, interrogation artifacts in SOS and BUA measurements are particularly pronounced in patients with abnormally increased soft tissue thickness that is commonly encountered in patients suffering from peripheral edema due to cardiovascular, renal, or hepatic disorders. Previous work failed to recognize that soft tissue swelling or fluctuations in soft tissue thickness in patients with peripheral edema changes the acoustic properties of the interrogated tissue. The inventors were the first to recognize that changes in ultrasonic properties of interrogated tissue induced by local or generalized soft tissue swelling or fluctuations in soft tissue physiology can reduce short-term and long-term in vivo precision of SOS and BUA measurements. The inventors were also the first to recognize that soft tissue swelling induced changes in ultrasonic properties of interrogated tissue overlying bone can be particularly significant in patients with edema undergoing diuretic or other types of medical treatment of edema with resultant fluctuations in soft tissue physiology or homeostasis.

For example, FIG. 1A through FIG. 1D illustrate tissue structure variations that can lead to acoustic variations in ultrasonic measurements due to changes in the interrogation path. Three types of tissue structure variations are present in such figures: 1) soft tissue structure heterogenity (as shown FIG. 1A through FIG. 1D), 2) dense tissue heterogeneity (compare for example FIG. 1A with FIG. 1C) and 3) tissue structure variations due to changes in the physiology of the tissue (compare FIG. 1A with FIG. 1C).

Figure 1B:
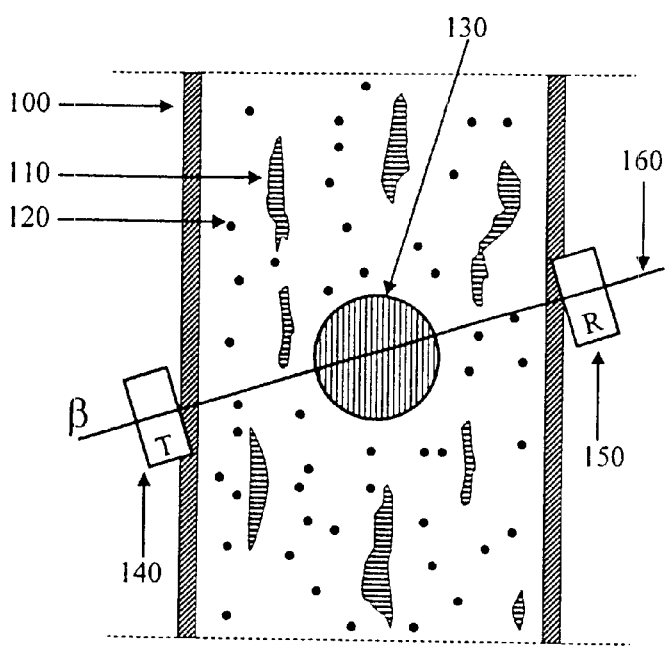

FIG. 1A and FIG. 1B show a tissue interrogated by an ultrasonic transducer (140; T) that transmits to an ultrasonic receiver (150; R) (or detector) at different transmission angles and with different axes of transmission. The axis of transmission is shown as $\alpha$ (or $\beta$) and has a transmission path from T to R. The transmission path passes through the tissue comprising skin (100), soft tissue (represented as white), locations of organized biomaterial (110) with acoustic properties different from that of the extracellular fluid in the soft tissue (e.g. differences in echogenicity, scatter, SOS, BUA, or reflection), amorphous, insoluble biomaterial deposits (120) with acoustic properties different from that of the extracellular fluid in the soft tissue (e.g. differences in echogenicity, scatter, SOS, BUA, or reflection), and dense tissue (130) with acoustic properties different from that of the extracellular fluid in the soft tissue. Comparison of the transmission paths of FIG. 1A and FIG. 1B shows that the transmission path traverses tissue structures with different acoustic properties. Hence, the ultrasonic measurements, such as the BUA or SOS, will not be the same depending on the transmission path, which can be changed by either varying the transmission angle or the axis of transmission in an anatomical region.

In addition, the transmission path from R to T traverses tissue structures with different acoustic properties in a spatial or time order that is different from the transmission path from T to R. Hence, the ultrasonic measurements, such as the BUA or SOS, will not be the same depending on the direction of the transmission path, which can be changed by either varying the direction of transmission in an anatomical region from T to R or from R to T.

Figure 1C:
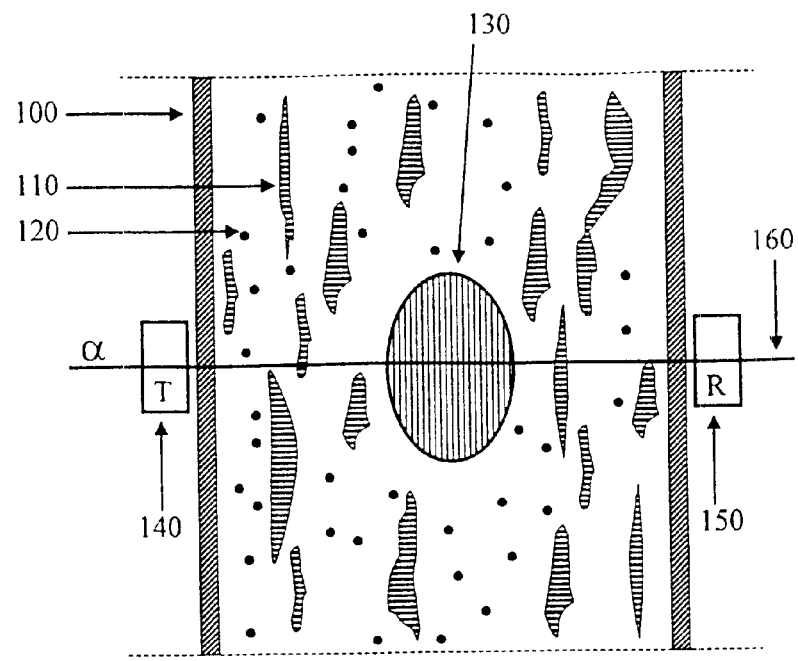
FIG. 1C and FIG. 1D show the same tissue as FIG. 1A and FIG. 1B in a different physiological state that changes the dimensions of the tissue and its underlying structure. The tissue is interrogated by an ultrasonic transducer (140; T) that transmits to an ultrasonic receiver (150; R) (or detector) at different transmission angles and with different axes of transmission as in FIG. 1C and FIG. 1D. The axis of transmission is shown as α (or β) and has a transmission path from T to R.
Figure 1D:
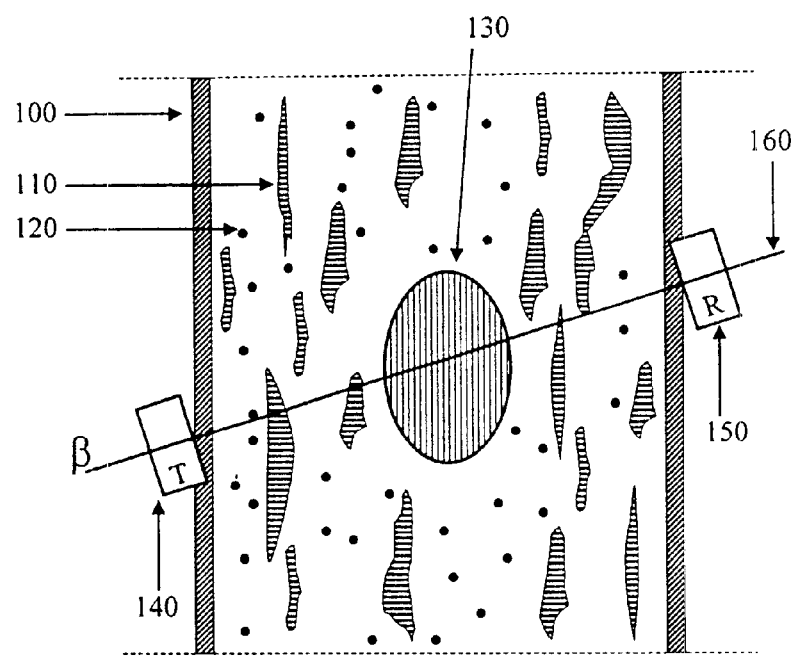
Figure 1E:
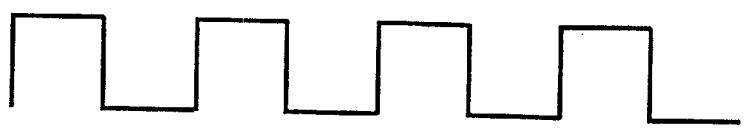
FIG. 1E shows received signals in such tissue in different physiological states and at different transmission angles.
Figure 1E:
Figure 1E:
Figure 1E:
Figure 1E:

FIG. 1C and FIG. 1D show the same tissue as FIG. 1A and FIG. 1B in a different physiological state that changes the dimensions of the tissue and its underlying structure. The tissue is interrogated by an ultrasonic transducer (140; T) that transmits to an ultrasonic receiver (150; R) (or detector) at different transmission angles and with different axes of transmission as in FIG. 1C and FIG. 1D. The axis of transmission is shown as $\alpha$ (or $\beta$) and has a transmission path from T to R. The transmission path passes through the tissue comprising skin (100), soft tissue (represented as white), locations of organized biomaterial (110) with acoustic properties different from that of the extracellular fluid in the soft tissue (e.g. differences in echogenicity, scatter, SOS, BUA, or reflection), amorphous, insoluble biomaterial deposits (120) with acoustic properties different from that of the extracellular fluid in the soft tissue (e.g. differences in echogenicity, scatter, SOS, BUA, or reflection), and dense tissue (130) with acoustic properties different from that of the extracellular fluid in the soft tissue. Comparison of the transmission paths of FIG. 1A and FIG. 1C shows that the transmission path traverses tissue structures with different acoustic properties due to the different physiological states in the tissue at different times. Hence, the ultrasonic measurements, such as the BUA or SOS, may not be the same depending on the physiological state of the interrogated tissue. Assessment of such differences in physiological states can be more accurately determined by either varying the transmission angle or the axis of transmission in an anatomical region. FIG. 1E shows received signals in such tissue in different physiological states and at different transmission angles.

By way of introduction, and not limitation of the various embodiments of the invention, the invention includes at least four general aspects:

1) an ultrasonic method of measuring speed of sound and broadband ultrasonic attenuation at predetermined, multiple transmission angles;
2) a method of correcting measured speed of sound and broadband ultrasonic attenuation for errors introduced by soft tissues interposed in the beam path between the ultrasonic transducers and the object to be measured using predetermined, multiple transmission angles;
3) an ultrasonic method reducing the artifacts from variations in tissue structure that alter ultrasonic properties or the ultrasonic transmission path by measuring ultrasonic properties at predetermined, multiple transmission angles; and
4) devices and systems to achieve or facilitate the methods 1 through 3.

These aspects of the invention, as well as others described herein, can be achieved using the methods and devices described herein. To gain a full appreciation of the scope of the invention, it will be further recognized that various aspects of the invention can be combined to make desirable embodiments of the invention. For example, the aspects 1 and 3 of the invention can be combined thereby improving reproducibility of measurements of SOS and BUA even further.

3.0 Automated System for Interrogating at Multiple Transmission Angles Using Ultransonic Transducers and Related Methods Predetermined Axis of Transmission and Automated Multiple Transmission Angle System The present invention includes an ultrasonic system for ultrasonic interrogation of tissue at multiple transmission angles at single or multiple axes of transmission. The system is based, in part, on improving ultrasonic measurements by creating a desired axis of transmission or spatial relationship typically between two ultrasonic transducers and their transmission paths (or reception paths). In the preferred embodiments, the ultrasonic system is adapted to interrogate dense tissues to measure either broadband ultrasonic attenuation or speed of sound.

Typically, such a system includes a first ultrasonic transducer with an axis of transmission in common with a second ultrasonic transducer. The axis of transmission is usually through a portion of a dense tissue and usually the transducers are not permanently fixed but are capable of being repositioned to a predetermined or desired location. In addition, in some embodiments the positioner may also vary the transmission angle of the transducer(s) in a predetermined fashion while maintaining an axis of transmission in common between the two transducers. In other embodiments, especially single transducer unit embodiments, the transmission angle may vary and no axis of transmission is present or maintained.

Typically, the two transducers can be aligned (e.g. mechanically aligned) to have a common axis of transmission. In such situations, the transducers will be generally directed at each other to receive signals from each other. In some applications, the transducers may not have an axis of transmission in common but are instead arranged to each have a predetermined axis of transmission, wherein each transducer may send signals that can be received by the other transducer without having a common axis of transmission. The axis of transmission for each transducer will have an angle of transmission associated with it that can be varied. Preferably, the transducers are adapted for BUA or SOS or both.

Alternatively, tandem transducers can be used wherein each tandem transducer is comprised of 1) a transducer designed for A scan or B scan, and 2) a transducer designed for either broadband ultrasonic attenuation or speed of sound measurements or both. It is understood that a tandem transducer can be paired so that, for instance, the broadband ultrasonic transducer in the first tandem transducer transmits signals and the broadband ultrasonic transducer in the second tandem transducer receives signals.

In some embodiments the axis of transmission of each transducer is predetermined or selected in advance of, or during, transmission or reception of, ultrasonic waves. The axis of each transducer can be adjusted or directed to permit either 1) a partial overlap (typically less than about a twenty percent overlap in the acoustic field), 2) a substantial overlap (typically more than about a twenty percent overlap in the acoustic field), 3) a complete overlap (typically more than about a ninety percent overlap in the acoustic field) or 4) no overlap (typically less than about a five percent overlap in the acoustic field) with an axis of transmission of another transducer.

Partial overlap of each axis of transmission facilitates interrogation of tissue from two separate interrogation sites while permitting 1) interrogation of tissue by a single transducer (where there is no substantial overlap of each axis of transmission) or 2) interrogation of tissue by two or more transducers (where there is a partial overlap of each axis of transmission). Typically, the sites of interrogation are at least about 1 cm apart, often at least about 4 cm apart and sometime 6 cm or more cm apart. Transducers at interrogation sites can also be positioned on different faces or sides of a tissue to be interrogated (e.g. on the medial and lateral portion of an appendage). In many of these embodiments the transducers receive signals from each other. Preferably, tandem transducers are used that are adapted or programmed to receive signals from each other. The invention, however, is not limited to such embodiments and a plurality of predetermined axes of transmission for plurality of transducers can be established, wherein the transducers are either adapted to receive signals from other transducers in the system or the signals received and transmitted by each transducer are separately processed. Similarly, substantial or complete overlaps can be achieved if so desired in some embodiments.

Multiple transducers can also be used to create multiple overlaps between each axis of transmission. Each axis of transmission can overlap the same area in a tissue to permit interrogation of the tissue by multiple transducers from separate interrogation sites. For example, multiple transducers can be directed to have overlapping axes of transmission to form a desired interrogation volume or path in the tissue (e.g. an interrogation volume substantially shaped like a column or cone). Multiple transducers creating common interrogation volumes from separate interrogation sites using overlapping axes of transmission can improve resolution of internal structures or surfaces.

Without limiting aspects of the invention to a particular mechanism of action, multiple transmission angles, multiple axes of transmission and common interrogation volumes can give rise to enhanced, or more precise, ultrasonic measurements due to any one or combination of the following factors. In addition, these factors may be applied to embodiments of the invention with a single transducer unit or multiple transducers.

One, reduction in interference and scatter by comparing ultrasonic properties (e.g. ultrasonic data in the form of A scan or B scan) from each transducer and selecting the data with the least amount of interference to use in a reconstruction, map or ultrasonic analysis of the tissue.

Two, reduction in ultrasonic wave attenuation (not necessarily broadband ultrasonic attenuation) by comparing ultrasonic properties (e.g. ultrasonic data in the form of A scan or B scan) from each transducer and selecting the data with the least amount of attenuation to use in a reconstruction, map or ultrasonic analysis of the tissue.

Three, signal averaging between each transducer participating in multiple transmission angles, multiple axes of transmission and common interrogation volumes. Such signal averaging would typically account for the different interrogation sites of each transducer, the amount of axis of transmission overlap or selection of the most accurate data generated for each transducer or a combination thereof.

Four, unreceived, anticipated signal analysis, which entails analysing the absence of, or change in, signals that are anticipated or predicted to be received by a detector. The absence or change in signals will be indicative of the presence of structures in the path that remove or alter the transmitted ultrasonic signal.

In addition, interference, scattering and attenuation, as well as other sources of error, may vary between transducers because the transducers are located at separate interrogation sites offering different interrogation paths with varying levels of interference, scattering, attenuation, etc. This is based, in part, on the property of ultrasonic hysteresis meaning either 1) the path of an ultrasonic signal transmitted by a transducer through an object of varying compositions with a heterogenous organization returns to the transducer by a different path and with an altered wave form or 2) the path of an ultrasonic signal transmitted by a first transducer through an object of varying compositions with a heterogenous organization will be received by a second transducer by a different path and with an altered wave form compared to an ultrasonic signal transmitted by the second transducer through the same object and received by the first transducer.

For example, a model interrogation site has layers, from the first side of the object to the second side of the object, of A, B, and C. Wherein layer A, B and C all have different speed of sound constants, and different microstructures contributing to interference, attenuation and scatter. A signal moving from A to C and back again will have traveled a different path than a signal moving from C to A and back again. A transducer that transmits and receives signals at an interrogation site on the surface of layer A will receive a different set of signals compared to a transducer that transmits and receives signals at an interrogation site on the surface of layer C. Alternatively, a signal moving from A to C will have traveled a different path than a signal moving from C to A. A transducer that receives signals at an interrogation site on the surface of layer C from a transducer sending signals from layer A will receive a different set of signals compared to a transducer that receives signals at an interrogation site on the surface of layer A from a transducer located on the surface of layer C. Consequently, the received signals will have different properties dependent on the path taken through the object. In addition, these observations may be applied to embodiments of the invention with a single transducer unit or multiple transducers.

The different interrogation paths of each transducer offers the ability to sample the data from each path and select the best or appropriate data using defined selection criteria, thereby reducing the source of error or enhancing interrogation of the tissue. For example, in an interrogation of a tibial region a transducer placed on the anterior surface of the tissue may have a sharp and intense reflective surface 1 cm below the surface of the skin indicating bone. The same interrogation site will have little ability to interrogate the muscle "behind" the bone. A second transducer positioned at a second interrogation site on the posterior region of the same tibial region will offer relatively greater ability to interrogate the muscle "behind" the bone compared to the first interrogation site since the muscle is now interrogated using ultrasonic waves that have not been deflected off or attenuated by bone. Data analysis that selects and combines data from each interrogation, and optionally including signal averaging, can be used to generate a reconstruction, map, or ultrasonic analysis of the tissue. Such positioning methods and devices can be used with BUA or SOS, as well as imaging techniques.

Methods and devices used to generate multiple transmission angles, multiple axes of transmission and common interrogation volumes, as well as other methods and devices herein, can aid in producing ultrasonic assessments of the tissue, anatomic maps of the tissue or imaging of the tissue. It can also be used in conjunction with invasive procedures as a guide or monitor of the progress of the procedure, such as catheterization, trocar based procedures or other types of surgery.

Some examples of different embodiments of tandem transducers related to an axis of transmission are as follows:

1) a common axis of transmission with each transducer substantially orthogonal to the tissue plane,
2) a common axis of transmission with each transducer not substantially orthogonal to the tissue plane (e.g. a first transducer has a transmission angle 75 degrees and a second transducer has a transmission angle of 105 degrees),
3) a predetermined axis of transmission for a first transducer and a second transducer, wherein there is a partial overlap of each predetermined axis of transmission of the first and second transducer and each transducer is substantially orthogonal to the tissue plane, and
4) a predetermined axis of transmission for a first transducer and a second transducer, wherein there is a partial overlap of each predetermined axis of transmission of the first and second transducer and each transducer is not substantially orthogonal to the tissue plane.

In addition, some examples of different embodiments of a plurality of transducers (e.g., 2, 3, 4, 5, 6 or more) related to a desired interrogation volume are as follows:

1) a desired interrogation volume generated from a common axis of transmission with each transducer substantially orthogonal to the tissue plane,
2) a desired interrogation volume generated from a plurality of transducers each having an axis of transmission at a predetermined angle with respect to the other transducers or the tissue plane (e.g. a first transducer has a predetermined angle of 60 degrees with respect to a second transducer and a predetermined angle of 120 degrees with respect to a third transducer), and
3) a desired interrogation volume generated from a predetermined axis of transmission for a first transducer and a second transducer, wherein there is a partial overlap of each predetermined axis of transmission of the first and second transducer and each transducer is substantially orthogonal to the tissue plane.

Generally, the system will include an x, y positioner that engages the first ultrasonic transducer and the second ultrasonic transducer to locate each transducer in the appropriate position on the object to be interrogated. The x,y positioner can be designed to vary the transmission angle of the transducer(s). Usually, the x, y positioner positions the first ultrasonic transducer and the second ultrasonic transducer while generally maintaining the axis of transmission. The x,y positioner can be designed to include positioning of each transducer independently or positioning of each transducer while simultaneously maintaining a common axis of transmission. The x, y positioner can position the ultrasonic transducer at a desired location along the x axis and y axis of the system. Typically, the x axis is the horizontal axis and the y axis is vertical axis.

A computational unit can be included in the system to manage ultrasonic measurements. Typically, the computational unit is designed to manage ultrasonic signal transmission and reception of the first ultrasonic transducer and the second ultrasonic transducer. It may also be designed to optionally control movement of the x, y positioner. By monitoring signal transmission and reception the computational unit can instruct the x, y positioner to appropriately locate the transducers in order to achieve the desired relationship between the axis of transmission of each transducer. For example, one method of instructing a positioner and interrogating a tissue is based on predetermined multiple angles of interrogation with respect to common anatomical region in the tissue. In such case, all transmission paths substantially pass through such point.

In many instances the computational unit can be programmed to instruct the x, y positioner to establish a common axis of transmission between the two transducers. As described herein, this is a particularly useful embodiment for broadband ultrasonic attenuation and speed of sound measurements in the human heel. It is also contemplated to use such a system in other anatomical regions where ultrasonic measurements would benefit from controlled or predetermined x, y positioning with two or more probes (e.g. imaging) along with multiple interrogation paths. Typically, the computational unit is programmed to generate multiple transmission paths or angles using either A scan or B scan data or both. Multiple transmission paths can also be generated using other ultrasound parameters, e.g. flow information acquired with ultrasonic contrast agents.

Another embodiment of the invention relates to methods of interrogating a tissue, generating multiple interrogation paths at an anatomical region and instructing a positioner to change the angle of transmission of the transducer(s). Multiple transmission paths are generated from data obtained by interrogating the tissue at a first transducer(s) transmission angle(s) ($n_1$). This can be done using any ultrasonic measurement, such as A scan or B scan or both. A clinical measurement is then made at the first transmission angle $n_1$. Any clinical measurement can be used including, SOS, BUA, echogenicity, reflective surfaces, and ultrasonic images. Multiple transmission paths can also be used to guide a surgical procedure. The process of interrogating with multiple transmission angles can be repeated at subsequent transmission angles ($n_1$, $n_2$, ... ). Optionally, the ultrasonic measurements can be can be compared at different angles or averaged and stored in the computational unit. The process of obtaining measurements at multiple angles can be repeated until the desired data is obtained. Typically, the positioner moves the transducer in increments until the desired predetermined transmission angle has been reached and the tissue is interrogated for clinical measurement, such as speed of sound or broadband ultrasonic attenuation measurement. Such methods can be adapted as instructions for components of a monitoring system that form a computer program product.

A system that includes one, two, or more ultrasonic transducers, an x,y positioner for generating multiple transmission angles and a computational unit for signal management and transducer positioning offers a number of advantages. First, transducer positioning for multiple transmission angles can be automatically established without significant operator intervention, as well as with operator direction to a desired position. Second, accuracy and reproducibility of transducer positioning and generation of transmission angles can be improved by appropriately programming the computational unit. Finally, adjustments to transducer transmission angles during interrogation can be accomplished with minimized interruption of the interrogation process.

The system may optionally include a z positioner that engages and/or positions at least one or more ultrasonic transducers. Preferably, both transducers can be positioned in the z dimension by the z positioner. The z positioner changes the distance of transmission along the axis of transmission between the first ultrasonic transducer and the second ultrasonic transducer. Typically, it changes the distance between the transducer and the interrogation with minimal compression of the interrogated tissue. A pressure sensor can be included on the surface of the transducer or other location to monitor transducer pressure against the interrogated tissue. The pressure sensor can be part of control unit to regulate the amount of transducer pressure at the interrogation site by adjusting the transducer location in the z dimension with the z positioner. If desired, an electronic feedback loop can be included to adjust the transducer position in the z dimension in response to changes in pressure, which could arise from patient movement, tissue swelling or other factors that contribute to changes in transducer pressure. The z positioner can position the ultrasonic transducer at a desired location along the z axis of the system. Typically, the z axis is the axis perpendicular to the x axis which is the horizontal axis, and the y axis is the vertical axis. The z positioner moves the transducer(s) along the z-axis further or closer to the surface of the anatomical location.

The system may optionally include, or be designed as a dedicated device, to achieve speed of sound or broadband ultrasonic attenuation measurements or both. Typically, in such a system the computational unit can estimate speed of sound or broadband ultrasonic attenuation in an interrogated tissue. Preferably, the computational unit can correct the speed of sound or broadband ultrasonic attenuation measurements for errors generated by soft tissue effects. The database may also be comprised of factors related to empirical measurements of soft tissue and broadband ultrasonic attenuation, including historic patient records for comparison.

The x, y positioner included in the system can be any positioner that can accurately position a transducer and maintain the transducer position during interrogation. The x, y positioner can be those known in the art of positioning devices or those developed in the future or disclosed herein. In selecting an x, y positioner the following features should considered and incorporated into the x, y positioner design depending on the application: 1) ease of movement of the positioner preferably with automated control, 2) integration of the positioner into a computer control system, 3) accuracy of positioning (preferably within about ±5 mm, more preferably about ±1 mm and most preferably about ±0.05 mm), 4) speed of achieving a new position should typically be less than 2 to 4 seconds, and 5) ability of the x, y positioner to either locate one transducer or two transducers. It is understood that the x, y positioner may be configured in many arrangements. For instance, the x, y positioner may designed as one positioning system that moves each transducer concurrently or as two x, y positioners that move each transducer independently yet in a coordinated fashion with respect to each transducer. The x, y positioner can be manually controlled, operator computer controlled, or automatically controlled with minimal or no operator intervention or a combination thereof. Preferably, the system is capable of all three modes of operation. If a manual mode is incorporated into the device, the x, y positioner typically includes a grip to manually direct the first and second transducers over a desired anatomic region. Positioners in the art may used as well, such as those provided by Newport (Irvine, Calif.), including stages for rectilinear motion.

In one embodiment the x, y positioner can comprise a frame to maintain the axis of transmission between the first and second ultrasonic transducers. In this embodiment the x, y positioner maintains a "fixed" axis of transmission. Typically, these types of positioners can be less expensive to operate and robust under a variety of clinical conditions because the axis of transmission is fixed, typically during manufacture or in an adjustment protocol. Thus, the x, y positioner is not required to locate the transducer with respect to one another since this is predetermined. Instead the x, y positioner can be primarily designed to locate the transducer in tandem with a fixed common axis of transmission in relation to the anatomic region of interrogation. Typically, the frame engages an x track and the x track engages a y track, thereby an operator can move the first and second ultrasonic transducers manually in either an x or y dimension or combination thereof with respect to an anatomic region. It is understood, however, that such tracks could also be located on separate frames without a fixed common axis of transmission between the two transducers and that a common axis of transmission could be established. The x,y positioner can be designed to accommodate an appendage. Typically, the appendage is held in a predetermined position in the ultrasonic system relative to the x,y positioner. Preferably, the x,y positioner is automatically controlled by the computational unit. In one arrangement, the computational unit instructs an x servo-motor to drive the first ultrasonic transducer and second transducer in the x dimension and a y servo-motor to drive the first ultrasonic transducer and second transducer in the y dimension.

Figure 2A:
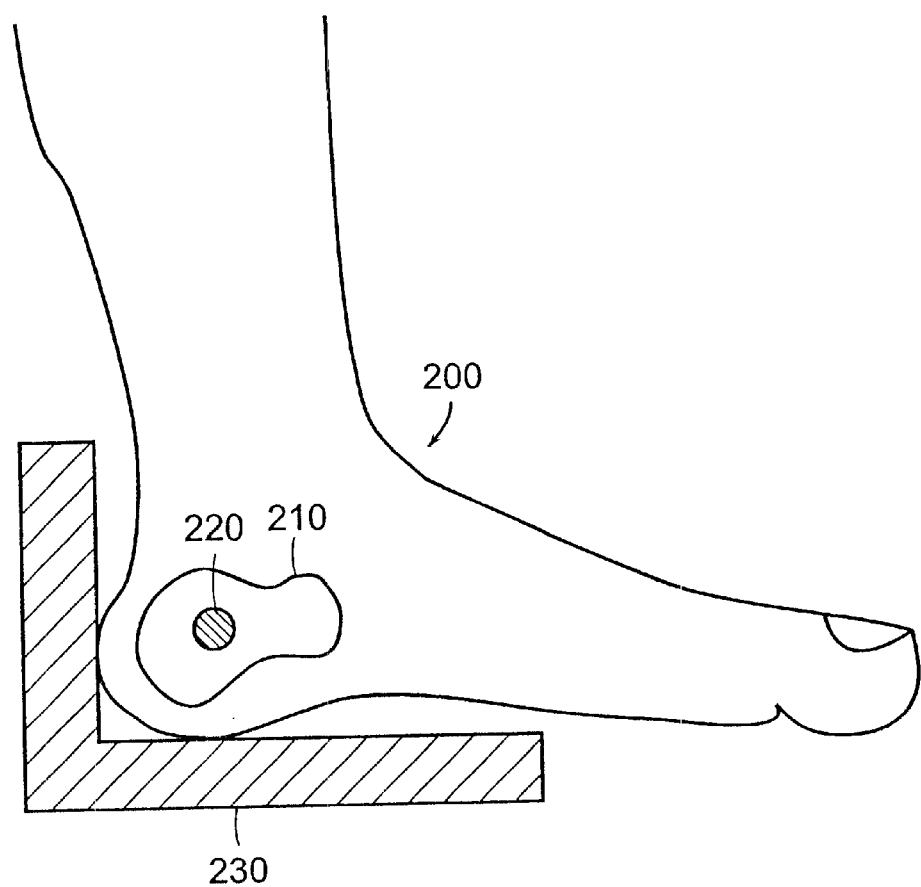
FIG. 2A shows an example of a typical prior art device for measuring the speed of sound or broadband ultrasonic attenuation in a healthy non-edematous patient.

FIG. 2A shows an example of a typical prior art device for measuring the speed of sound or broadband ultrasonic attenuation in a healthy non-edematous patient. The position of the patient's foot 200, of the calcaneus 210, and of the ultrasonic interrogation site 220 are fixed with respect to the device frame 230.

Figure 2B:
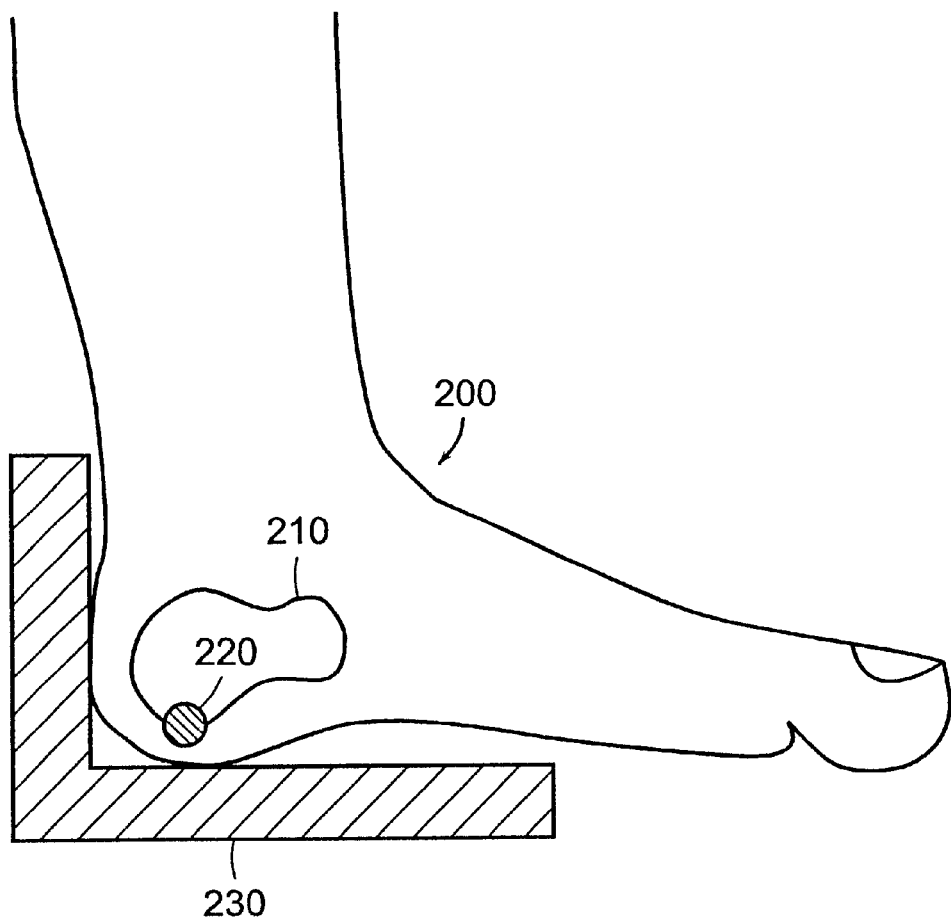
FIG. 2B shows an example of a typical prior art device for measuring the speed of sound or broadband ultrasonic attenuation in a patient with peripheral edema. Edema increases the thickness of the soft tissue inferior and posterior to the calcaneus.

FIG. 2B shows an example of a typical prior art device for measuring the speed of sound or broadband ultrasonic attenuation in a patient with peripheral edema. Edema increases the thickness of the soft tissue inferior and posterior to the calcaneus. Since the position of the ultrasonic interrogation site 220 is fixed relative to the device frame 230, a more inferior and posterior region is measured within the calcaneus 210 when compared to FIG. 2A that is even partially outside the calcaneus 210.

By interrogating at multiple transmission angles as described herein, changes in probe position, such as those described in FIG. 2A and FIG. 2B, can be compensated for or reduced (see FIG. 3C through FIG. 3G).

Figure 3A:
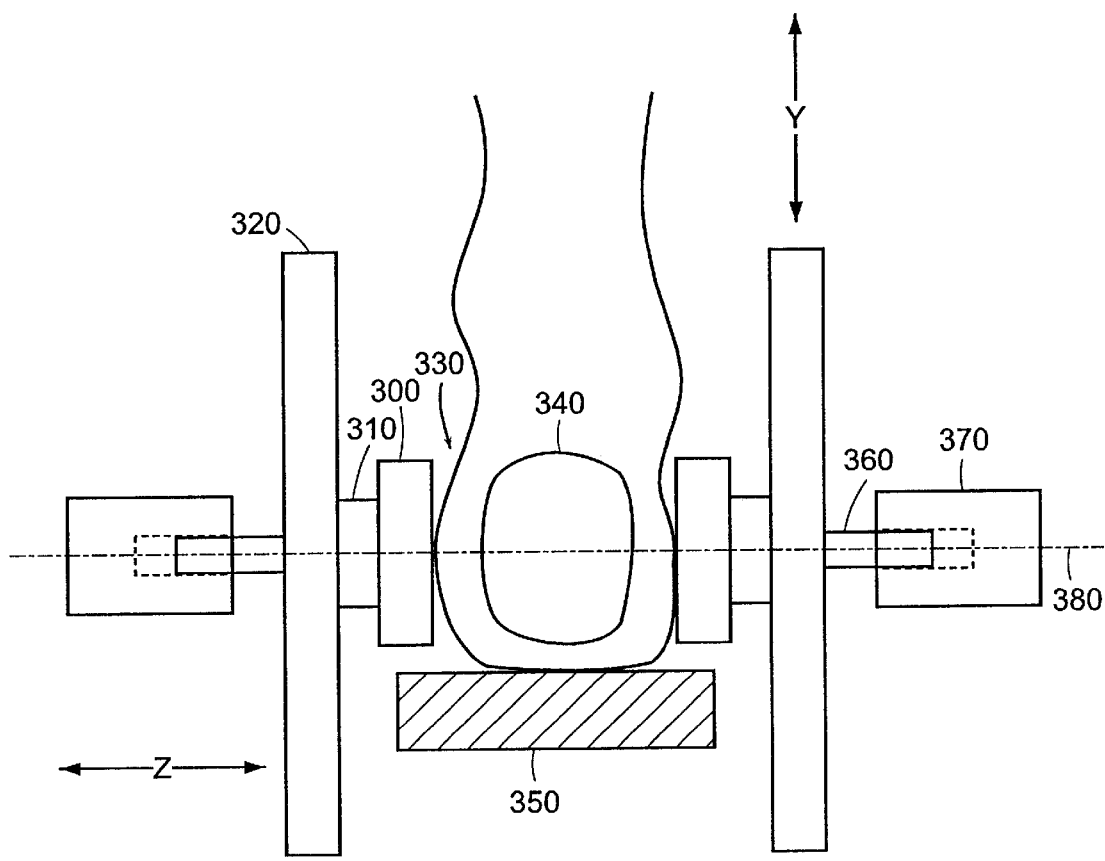
FIG. 3A shows another embodiment of the invention comprising two ultrasonic transducers 300 attached to an x-positioner 310 and a y-positioner 320. The heel 330 and the calcaneus 340 are seated on a foot holder 350. The ultrasonic transducer 300 is brought in contact with the heel 330 using a z-positioner member 360 that can move in and out of a frame 370 continuously or in a stepwise fashion. The ultrasonic transmission axis 380 is also shown.

FIG. 3A shows an embodiment of the invention comprising two ultrasonic transducers 300 attached to an x-positioner 310 and a y-positioner 320. The heel 330 and the calcaneus 340 are seated on a foot holder 350. The ultrasonic transducer 300 is brought in contact with the heel 330 using a z-positioner member 360 that can move in and out of a frame 370 continuously or in a stepwise fashion. The ultrasonic transmission axis 380 is also shown.

Figure 3B:
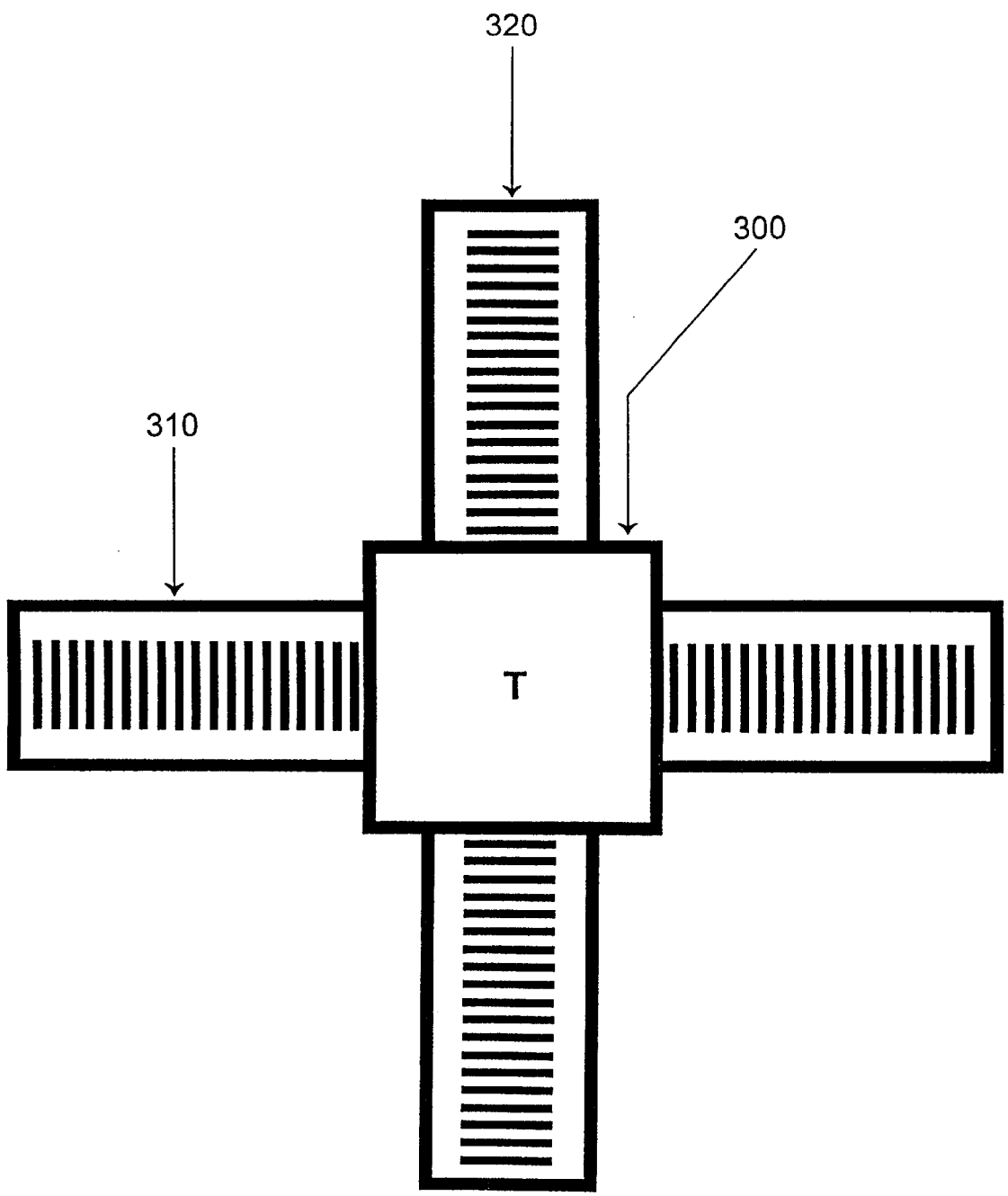
FIG. 3B is a side view of the ultrasonic transducer (T) 300, the x-positioner 310, and the y-positioner 320 shown in FIG. 3A showing the tracks of each postioner. Typically, one positioner will engage the other positioner to permit x, y movement either concurrently (moving in both directions simultaneously) or sequentially (moving in one dimension first and then in a second dimension).

FIG. 3B is a side view of the ultrasonic transducer (T) 300, the x-positioner 310, and the y-positioner 320 shown in FIG. 3A showing the tracks of each postioner. Typically, one positioner will engage the other positioner to permit x, y movement either concurrently (moving in both directions simultaneously) or sequentially (moving in one dimension first and then in a second dimension).

Figure 3C:
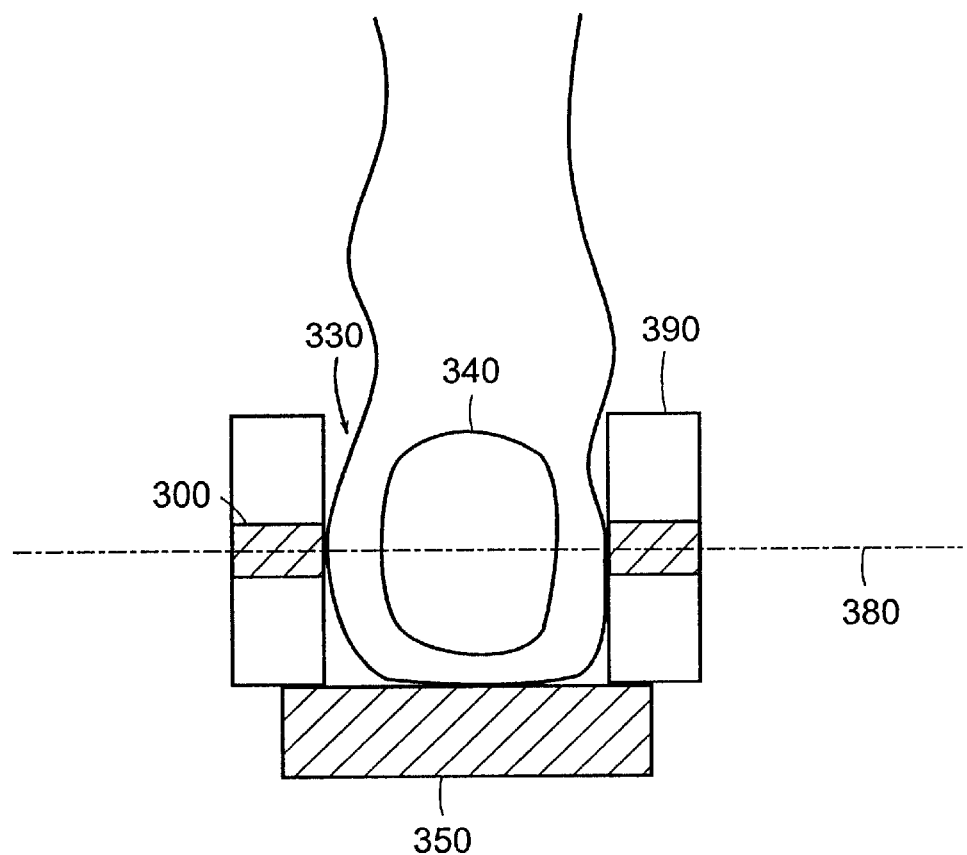
FIG. 3C shows another embodiment of the invention. The ultrasonic transducers 300 are attached to a positioning system 390 that affords movement of the transducers in x, y-, and z-direction, as well as angulation of the transducers 300 and the resultant ultrasonic transmission axis 380. The angulation position of the transducers 300 and the ultrasonic transmission axis 380 is substantially zero.

FIG. 3C shows another embodiment of the invention. The ultrasonic transducers 300 are attached to a positioning system 390 that affords movement of the transducers in x, y-, and z-direction, as well as angulation of the transducers 300 and the resultant ultrasonic transmission axis 380. The angulation position of the transducers 300 and the ultrasonic transmission axis 380 is substantially zero.

Figure 3D:
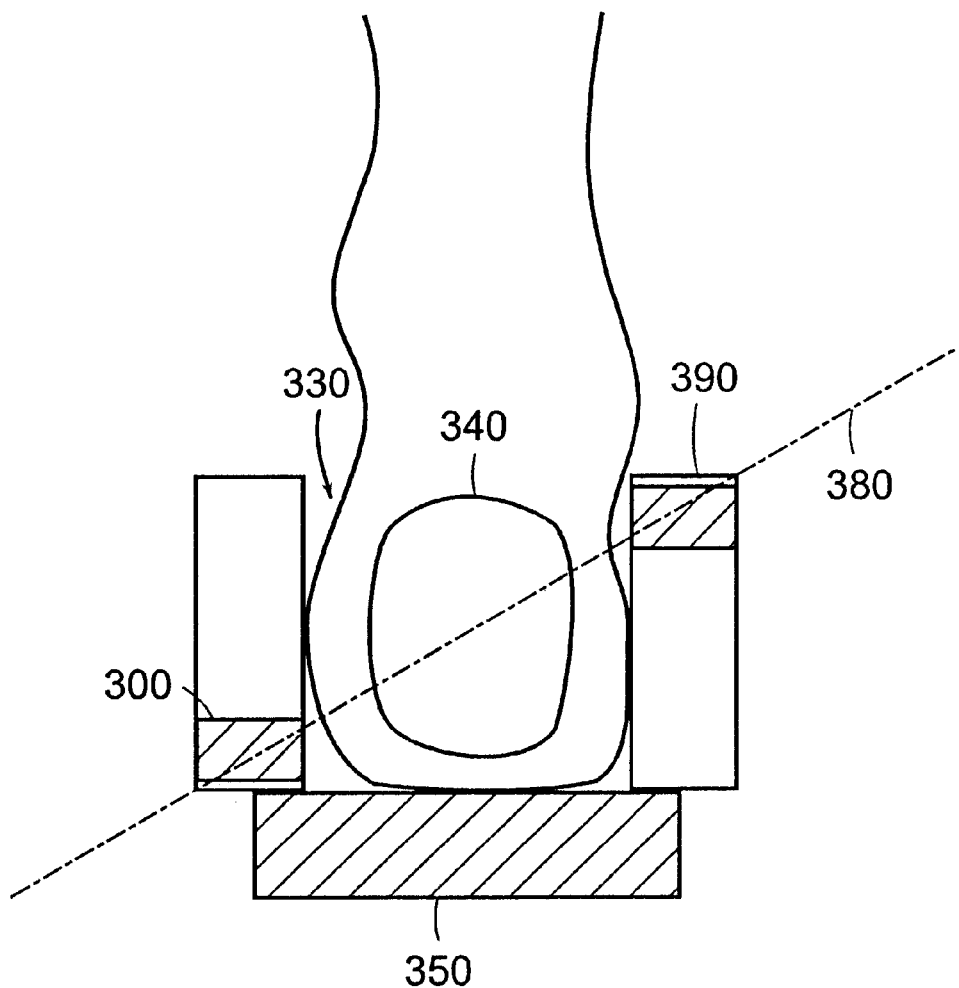
FIG. 3D shows the ultrasonic transducers 300 attached to a positioning system 390 that affords movement of the transducers in x, y-, and z-direction, as well as angulation of the transducers 300 and the resultant ultrasonic transmission axis 380. The angulation position of the transducers 300 and the ultrasonic transmission axis 380 is substantially different from zero.

FIG. 3D shows the ultrasonic transducers 300 attached to a positioning system 390 that affords movement of the transducers in x, y-, and z-direction, as well as angulation of the transducers 300 and the resultant ultrasonic transmission axis 380. The angulation position of the transducers 300 and the ultrasonic transmission axis 380 is substantially different from zero.

Figure 3E:
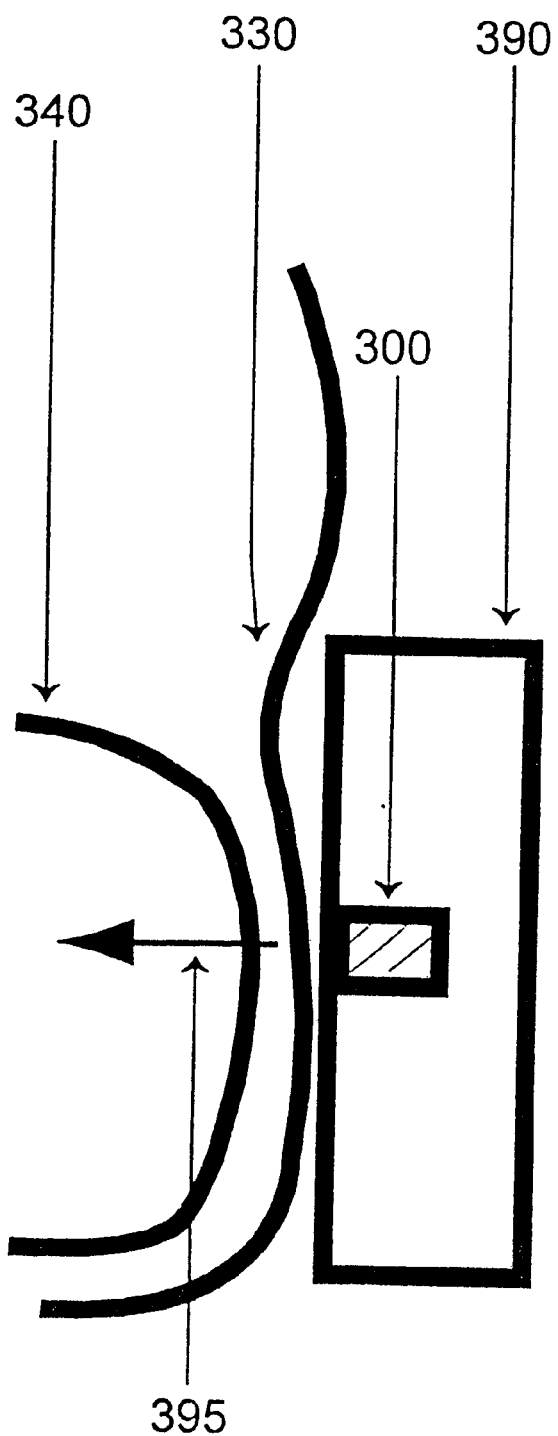
FIG. 3E shows an expanded view of the embodiment presented in FIGS. 3A–D. The ultrasonic transducer 300 is attached to a positioning system 390 that affords movement of the transducers in x, y-, and z-direction, as well as angulation of the transducers 300. The ultrasonic beam 395 has substantially zero angulation.

FIG. 3E shows an expanded view of the embodiment presented in FIGS. 3A–D. The ultrasonic transducer 300 is attached to a positioning system 390 that affords movement of the transducers in x, y-, and z-direction, as well as angulation of the transducers 300. The ultrasonic beam 395 has substantially zero angulation.

Figure 3F:
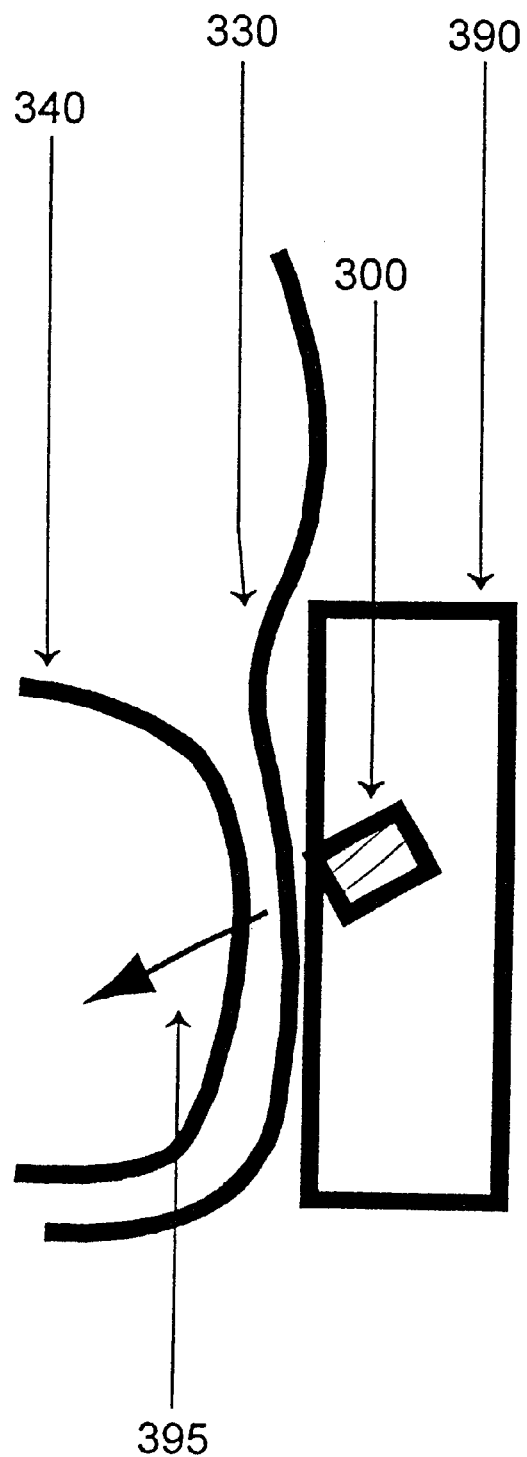
FIG. 3F shows an expanded view of the positioning system 390 and the ultrasonic transducers 300 with inferior angulation of the ultrasonic beam 395.

FIG. 3F shows an expanded view of the positioning system 390 and the ultrasonic transducers 300 with inferior angulation of the ultrasonic beam 395.

Figure 3G:
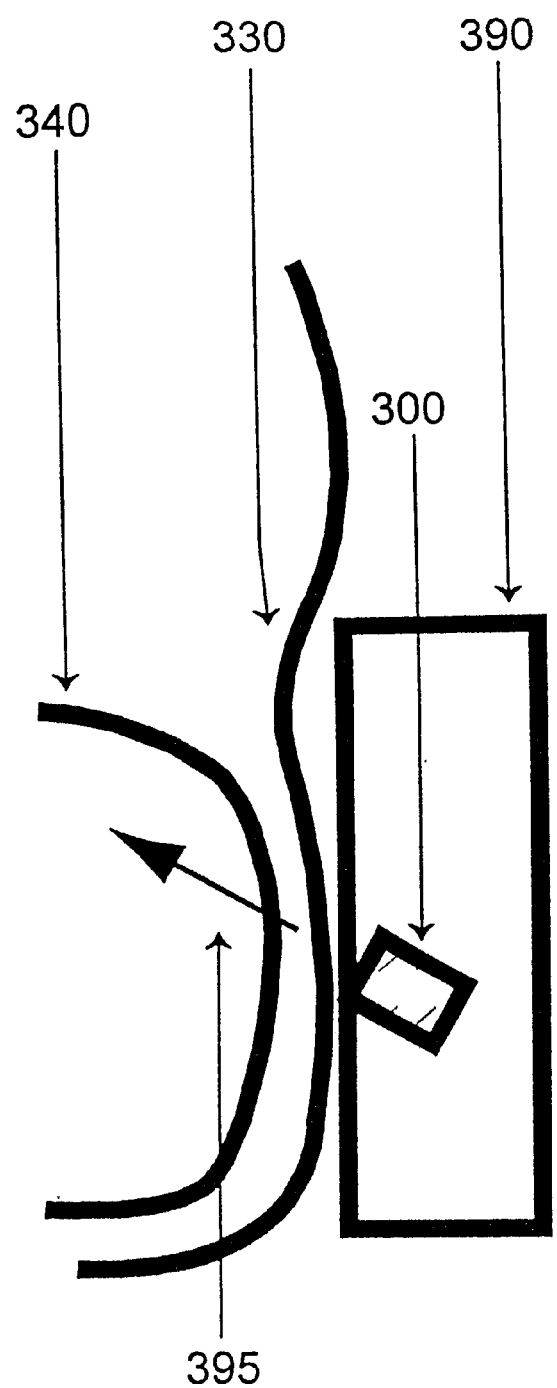
FIG. 3G shows a magnification view of the positioning system 390 and the ultrasonic transducers 300 with superior angulation of the ultrasonic beam 395.

FIG. 3G shows a magnification view of the positioning system 390 and the ultrasonic transducers 300 with superior angulation of the ultrasonic beam 395.

4.0 Methods for Generating Multiple Transmission Angles

The invention also includes an ultrasonic method for determining broadband ultrasonic attenuation or speed of sound measurements in dense tissues, comprising:

interrogating a patient's tissue with at least a first ultrasonic transducer unit at a first transmission angle and a second ultrasonic transducer unit at a second transmission angle, wherein said first ultrasonic transducer unit and said second ultrasonic transducer unit are a) adapted for either 1) broadband ultrasonic attenuation or 2) speed of sound measurements or both and b) have an angle of least about 150 degrees between said first ultrasonic transducer unit and said second transducer unit, interrogating said patient's tissue with said first ultrasonic transducer unit at a third transmission angle and said second ultrasonic transducer unit a fourth transmission angle while maintaining an angle of at least about 150 degrees between said first transducer unit and said second transducer unit, and determining dense tissue broadband ultrasonic attenuation, dense tissue speed of sound or both for said tissue; wherein said determining step generates a dense tissue broadband ultrasonic attenuation value, dense tissue speed of sound value or both that is more indicative of broadband ultrasonic attenuation or speed of sound in dense tissue than in the absence of interrogating said patient's tissue with at least said first ultrasonic transducer unit at a third transmission angle and said second ultrasonic transducer unit a fourth transmission angle.

The invention also includes an ultrasonic system for determining broadband ultrasonic attenuation or speed of sound measurements in a tissue, comprising:

a transducer unit comprising at least a first ultrasonic transducer engaged with a first multiple transmission angle unit to controllably vary first transmission angles and a second ultrasonic transducer engaged with a second multiple transmission angle unit to controllably vary second transmission angles, wherein the first ultrasonic transducer unit and the second ultrasonic transducer unit are adapted for either 1) broadband ultrasonic attenuation or 2) speed of sound measurements or both, and a computational unit for controllably adjusting transmission angles of the first and second transducer; wherein the ultrasonic system will measure broadband ultrasonic attenuation value, speed of sound value or both if so desired.

Typically, transmission angles can differ in 1, 2, 3, 4, 5, 6, 7, 8, 9 or 10 degree increments or multiples thereof. Preferably, a series of transmission angles will be used, as measured with respect to the object plane, such as 90, 85, 80, 75, 70, 65 and 60 degrees. It will be readily apparent to those skilled in the art that transmission angles of 90, 95, 100, 105, 110, 115 and 120 degrees can also be used. In some embodiments, selection of the transmission angle is based on whether a common axis of transmission is desired.

In various embodiment of the invention, transmission angles can converge or diverge from an ultrasonic source or sources. Generally, there is seldom a limitation as to whether convergent or divergent transmission angles can be used in the invention. Some applications will, however, operate more effectively by selecting the appropriate angle arrangement. To retain a narrower field of interrogation, a single ultrasonic source can be used at relatively small divergent angles, such as no more than about a 20 to 30 degree total divergence in transmission angles. For a wider field of interrogation, multiple ultrasonic sources can be used with divergent angles. If a narrow field of interrogation is desired, multiple ultrasonic sources can be used with convergent transmission angles.

To vary transmission angles, typically a first pulse has a first transmission angle with respect to the object plane and a second pulse has a second transmission angle with respect to the object plane, wherein there is a predetermined divergent angle between the first and second pulse or a convergent angle between the first and second pulse. The predetermined divergent or convergent angles can be selected to improve the measurement of a ultrasonic parameters generated in A scan or B scan. The selection of transmission angles typically takes into account the depth in the field where the target reflective layer (or layers) is likely to be located (target reflective layer depth), the likely thickness of the target reflective layer (target reflective layer thickness), object composition and distances between ultrasonic sources (if multiple sources are used). Generally, the total range of transmission angles α will not be greater than 45 degrees, and preferably 30 degrees or less.

The divergent angle separates a first position and second position of an ultrasonic source or sources and the first pulse has a centered first axis of transmission and the second pulse has a centered second axis of transmission, wherein the first and second axis do not converge. Usually the divergent angle between the first and second pulse is between 5 to 90 degrees, and preferably between about 5 and 20 degrees.

The convergent angle separates a first position and second position of an ultrasonic source or sources and the first pulse has a centered first axis of transmission and the second pulse has a centered second axis of transmission, wherein the first and second axis converge. Usually the convergent angle between the first and second pulse is between 5 to 90 degrees, and preferably between about 5 and 20 degrees.

Different transmission angles can be accomplished by any method known, developed in the art or in the future or described herein. Typically, the invention includes three different methods (with the corresponding devices) for varying the transmission angle: 1) mechanically changing position of the transducer(s) with respect to the plane of the tissue, 2) providing multiple transducers with predetermined positions that correspond to predetermined transmission angles and 3) steering ultrasonic beams from multiple ultrasonic sources (typically arrays) with predetermined firing sequences. For cost effective production of devices only one of these methods will typically be used in a device. If more sophisticated devices are desired, such methods can also be combined to gain the benefit of the different methods.

To vary transmission angles using a mechanical device, typically the first and second pulses are from a first ultrasonic generator. The first generator has at least a first and a second position. The first and second position typically are mechanically connected. The generator is guided from the first position to the second position with a mechanical connection. The first and second position (or more positions for more transmission angles) for the ultrasonic generator can be connected using any connection that changes the transmission angle of the ultrasonic generator in an accurate and controllable fashion. Typically, a sweep through all of the desired positions, either in increments or continuously, should be completed within about 0.02 to 2 seconds, preferably within 200 to 500 milliseconds and more preferably within 20 to 200 milliseconds. These time values also apply to other methods of varying the transmission angle. Such a device can be mounted on or engaged by an x, y positioner to locate the tranducers at a desired anatomical region.

In one embodiment, the invention utilizes a mechanical connection comprising a mechanical motor that can oscillate a generator(s) at least once from the first to the second position (or more positions) in order to vary the transmission angle. This device can be used to create maps, identify anatomical landmarks, and measure BUA or SOS or other ultrasonic methods described herein. The mechanical motor typically provides a frame time of oscillation from 10 to 2500 ms. Any mechanical motor that can produce a position change in such a time frame in response to an electrical command signal and can be adapted for use in a hand-held probe can be preferably used to vary the transmission angle of ultrasonic generators, such as crystals or arrays of crystals. Such a device can be mounted on or engaged by an x, y positioner to locate the tranducers at a desired anatomical region.

In one design the mechanical motor has at least a first and second magnet to move the ultrasonic generator on a track, and the generator further comprises a magnetic source or magnetically attractive material that magnetically communicates with the first or second magnet to change the transmission angle. Magnetic switching of an ultrasonic generator position is particularly desirable because the magnet can be turned off and on relatively rapidly, and directed to change polarity relatively rapidly. Such magnetic systems can provide smooth position changes and relatively noise free performance. The track can be any mechanical device that directs the ultrasonic generator between positions. In some instances the track will comprise a groove that engages the ultrasonic generator and permits the ultrasonic generator to pivot around an axis to allow for the probe to sweep across the desired transmission angles. First and second magnet refers to magnets that can be used to move an ultrasonic source from a first to a second position. Magnets may be permanent or induced by applying an electric current to the appropriate electronic device. For example, an electric current can be applied to a wire arranged in a loop or coil-like configuration and the magnetic field created can be controlled by a predetermined electrical switch. The current induces a magnetic field that can be manipulated depending on the pattern of applied current or by the design of the coil or both. Additional magnets can be used for additional position for multiple placement.

In another embodiment, the invention utilizes permanently fixed ultrasonic generators with different, individual transmission angles to accomplish mapping, anatomical landmarks, BUA or SOS, or other ultrasonic methods described herein. Typically, a first pulse is from a first ultrasonic generator and second pulse is from a second ultrasonic generator, wherein the first and second ultrasonic generators are permanently fixed in a first and a second position. More than two ultrasonic generators can be used as well but usually not more than about 10 ultrasonic generators will be used in this embodiment, unless they are arrays of crystals.

In another embodiment, the invention utilizes predetermined patterns of ultrasonic source activation that result in different transmission angles to accomplish mapping, anatomical landmarks, BUA or SOS, or other ultrasonic methods described herein. For example, a predetermined pattern of ultrasonic source activation can comprise 1) a first series of trigger pulses that sequentially fires an array of ultrasonic crystals starting from a first end to a second end of the array and 2) a series of trigger pulses that sequentially fires the array from a second end to a first end of the array. The first series of pulses have a biased direction along a first portion of the field of the interrogated object, i.e. the beams are steered to one side of the field. This sequence of pulses can be repeated at different time frames in order to change the average transmission beam angle. Similarly, the second series of pulses have a biased direction along a second portion of the field of the interrogated object, i.e. the beams are steered to a second side of the field. This sequence of pulses can be repeated at different time frames in order to change the average beam angle. With linear arrays this method permits the use of either divergent or convergent transmission angles without mechanically moving the ultrasonic source to change the transmission angle. Averaged beams obtained by this method with different transmission angles can then be used to calculate BUA or SOS or other ultrasonic methods as described herein.

As part of the predetermined pattern of ultrasonic source activation, simultaneous triggering pulses may also be used in conjunction with sequential firing patterns. Simultaneous firing of the ultrasonic sources effectively provides a series of beams, which can be optionally averaged, to provide orthogonal probe position relative to a reference plane. When the ultrasonic source is orthogonal to the object/tissue plane, the transmission angle of simultaneously fired beams will be ninety degrees. If the probe has a non-orthogonal position, then the transmission will be more or less than ninety degrees. By comparing the signals generated from sequentially fired pulses to simultaneously fired pulses, the deviation from an orthogonal probe position can be calculated to accomplish mapping, anatomical landmarks, BUA or SOS or other ultrasonic methods described herein. Comparison of ultrasonic parameter (e.g. BUA or SOS) from the averaged signals of both the sequentially generated pulses and the simultaneously generated pulses will be indicative of the difference in tissue structure ascertained at different transmission angles. If so desired, this information can be transmitted back to the operator, for instance on a monitor, to alert the operator to tissue abnormalities or status. Once the operator has evaluated the results, the operator may instruct the system to adjust the probe to achieve orthogonal probe alignment for interrogation of that particular tissue.

The trigger pulses described herein can be particularly optimized to enhance measurement of BUA or SOS in vivo, such as in humans or other objects described herein. To steer a series of beams to create an averaged beam with a specific transmission angle, each ultrasonic crystal is triggered with a 1 $\mu$s to 500 $\mu$s delay between the firing of each crystal. By increasing the delay between firing each crystal, the depth of interrogation and the transmission angle of the averaged beam can be changed. Ultimately, depth of interrogation will be limited by the dimensions of the transducer near and far field (Bushberg, J. T., Seibert, J. A., Leidholdt, E. M., Boone, J. M., The Essential Physics of Medical Imaging 1–742 (1994)). The trigger pulses are timed to delay, such as an exponential delay, the firing of the crystals (e.g., crystals 1–5) over a 15 $\mu$sec time period. The firing sequence causes a delay across the array in order to steer to the target and provide an averaged beam (of five beams in this example) with a predetermined transmission angle, e.g. 75 degrees.

The invention also includes an ultrasonic method for generating an anatomic landmark for ultrasonic interrogation of an anatomical region, comprising:

a) positioning, if necessary, on the surface of a patient, with respect to an anatomical region, an ultrasonic transducer unit comprising either 1) a first ultrasonic transducer that can transmit and receive signals or 2) a pair of ultrasonic transducers wherein a first member of the pair is designed to transmit signals and a second member of the pair is designed to receive signals, and b) interrogating the anatomical region with the ultrasonic transducer unit at a first transmission angle, c) interrogating the anatomical region with the ultrasonic transducer unit at a second transmission angle, d) identifying an anatomic landmark in common with the signals obtained in the above steps in the anatomical region with an ultrasonic property of the anatomical region.

This ultrasonic method can further comprise the steps of comparing the location and axis of transmission of the ultrasonic transducer unit to the location of the anatomic landmark and positioning the ultrasonic transducer unit to produce an axis of transmission generally through the anatomic landmark. Steps a, b, and c can be optionally repeated. This can increase accuracy or permit close matching of observed landmarks with reference maps or landmarks. Each positioning step can be performed in relation to an anatomic landmark. The positioning steps are typically performed to generate an axis of transmission substantially through the anatomic landmark. Although the transmission axis can be in a predetermined coordinate or desired spatial relationship with respect to the landmark. The positioning steps can be performed to in relation to a reference anatomic landmark of the anatomical region that is stored in retrievable form a storage device.

In some embodiments, it will be desirable to generate anatomical maps and landmarks, as well as images, with signals from multiple transmission and detection angles. Generally, it will be desirable to place the probe in a position that is substantially orthogonal to the object plane. In many situations, it will be desirable to transmit a series of pulses at different transmission angles, usually about 5 to 10 degrees apart. This permits generating an image or alternatively a map or landmark from different interrogation paths.

EXAMPLES

The following materials and methods are exemplary of the materials and methods that can be used to achieve the results described herein. These examples are for illustrative purposes only, and are not to be construed as limiting the appended claims. One skilled in the art will readily recognize substitute materials and methods.

General Materials and Methods

In vivo ultrasonic measurements are performed using a prototype ultrasonic system capable of measuring speed of sound and broadband ultrasonic attenuation in the heel region. The device is also capable of measuring distances between different acoustic/tissue interfaces using A-scan technique.

The ultrasonic system consists of two ultrasonic sources mounted on a U-shaped plastic frame. A hinge is located in the center portion of the U-shaped plastic frame that allows for adjusting the distance between the ultrasonic transducers for each individual patient. The physical distance separating both transducers is registered for each patient using an electronic system that employs a potentiometer. The U-shaped plastic frame is connected to a plastic housing on which the patient can rest the fore- and mid-foot and in particular the heel comfortably. The ultrasonic sources are placed by the operator on the left and the right side of the foot in the heel region. An ultrasonic gel is used for acoustic coupling. The operator adjusts the frame and the attached ultrasonic sources visually so that they are flush with the skin and near perpendicular to the skin surface.

The ultrasonic system is designed with a central processing unit responsible for pulsing the ultrasonic transducer(s) and crystal(s), registering signals returned from the transducer, preamplification of the electronic signal, time gain compensation, signal compression, signal rectification, demodulation, and envelope detection, signal rejection, signal processing, analysis and display of SOS, BUA, and soft tissue and bone distance measurements. Transducers operate at a center frequency of 1 Mhz. However, transducer center frequency can be switched from 1 to 0.5 MHz. As the interrogation frequency of the micro-transducer decreases, generally, the ability to resolve reflective surfaces at deeper depths improves. The lower frequency is used in obese or edematous patients in whom tissue penetration with the 1 MHz probe is insufficient.

With each measurement the device registers initially the physical distance between both transducers. The device then measures (a) speed of sound, and (b) broadband ultrasonic attenuation. Broadband ultrasonic attenuation is calculated by subtracting the amplitude spectrum of a patient from one obtained in a reference material (e.g. de-gassed water).

As an alternative to ultrasonic distance measurements using A-scan technique, ultrasonic measurements can also be performed using another prototype system that is capable of two-dimensional image acquisition and display using B-scan technology in addition to SOS and BUA measurements. This ultrasonic system also uses two or more ultrasonic sources mounted on a hinged, U-shaped plastic frame. The physical distance separating both transducers is registered for each patient using an electronic system. After positioning of the patient and the transducers and application of the acoustic coupling gel, images are acquired in B-scan mode followed by SOS and BUA measurements. Images are displayed on a computer monitor attached to the scanner hardware.

All experiments performed on animal subjects (including humans) shall be performed with the highest ethical and medical standards and in accordance with the relevant laws, guidelines and regulations of the relevant governing jurisdiction(s) or professional association(s), including, where appropriate, compliance under 45 CFR 46 relating to United States federal policy for the protection of human subjects.

Example 1

Correction for Edema-Induced Changes in Ultrasonic Probe Position and Its Influence on In-Vivo Reproducibility of Calcaneal Speed of Sound and Broadband Ultrasonic Attenuation This example shows among other things that presence of peripheral edema does not only affect soft tissue thickness in the beam path thereby altering SOS and BUA directly but also affects ultrasonic probe position relative to the underlying bone. This examples documents that edema induced changes in ultrasonic probe position over the calcaneus and general variations in ultrasonic probe position over the calcaneus reduce short-term and long-term in vivo precision of SOS and BUA measurements.

Twenty patients with compromised cardiac performance and peripheral edema are selected for the study. SOS and BUA measurements are performed at different times in the day on two different days: In the morning on day 1 before 9 am and in the evening on day 2 after 6 pm. At each time interval, the degree of peripheral edema is assessed clinically by visual inspection and manual palpation. Using standard clinical techniques (see Bates et al., J. B. Lippincott, 1995), edema is subdivided into 5 grades:

0.) absent,
1.) slight,
2.) mild,
3.) moderate, and
4.) severe.

Ultrasonic measurements are performed in each patient using a first prototype ultrasonic system that is capable of SOS and BUA measurements. The patient's foot is secured in the ultrasonic device so that the heel of the foot rests on the heel pad of the device and the posterior aspect of the heel touches the back-wall of the instrument (see also FIGS. 2A and 2B). A small amount of acoustic coupling gel is applied to the skin and the ultrasonic transducers are placed against the skin at the measurement site. The position of the foot is not corrected for any changes in position induced by peripheral edema.

SOS and BUA measurements are then repeated using a second, different prototype ultrasonic system. This second system is capable of identifying the posterior contour and the inferior contour of the calcaneus on the B-scan images. Using these landmarks, the system positions the ultrasonic transducers automatically over a predefined region in the calcaneus, e.g. 1.5 cm anterior to the posterior calcaneal cortex and 1.5 cm superior to the inferior calcaneal cortex. In this fashion, the ultrasonic transducers are reproducibly positioned over the same measurement site in the calcaneus regardless of changes in the thickness of the posterior and inferior heel soft tissue pad.

In-vivo reproducibility between am and pm measurements is better with the second ultrasonic system that adjusts probe position relative to the posterior and the inferior cortex of the calcaneus than with the first prototype system with fixed probe position relative to skin/patient/heel surface.

Example 2

Correction for Edema-Induced Changes in Ultrasonic Probe Position and Its Influence on In-Vivo Reproducibility of Calcaneal Speed of Sound and Broadband Ultrasonic Attenuation Before and After Diuretic Therapy The experimental design used in this example is identical to that shown in Example 1. However, rather than assessing the influence of diurnal changes in tissue edema between morning and evening measurements, twenty patients with compromised cardiac performance and peripheral edema are studied prior to and two weeks after initiation of diuretic therapy.

The results show that in-vivo reproducibility of SOS and BUA is better when the ultrasonic system is capable of adjusting probe position relative to the anatomic landmarks, e.g. posterior and inferior cortex, of the calcaneus than with an ultrasonic system where the probe position is fixed relative to skin/patient/heel surface.

Example 3

Improvement in In-Vivo Reproducibility of SOS and BUA Measurements of the Calcaneus Using Variable Ultrasonic Transmission Angles This example shows among other things that the in vivo reproducibility of ultrasound measurements of SOS and BUA can be improved by using variable transmission angles.

Twenty patients with osteoporosis are selected for the study. Patients undergo SOS and BUA measurements of the heel on two separate days, baseline and repeat examination 24 hours later.

Using a first prototype ultrasonic system, SOS and BUA are measured. The first prototype system is not capable of B-scan imaging and transmission of ultrasonic signals at multiple transmission angles.

The patients are then scanned using a second prototype ultrasonic system. The second ultrasonic system is capable of ultrasonic image acquisition and display using B-scan mode in addition to SOS and BUA measurements. Furthermore, the ultrasonic system is also capable to transmit and receive signals at different transmission angles (a) from the same position, and (b) from different positions. Using multiple image acquisitions at multiple transmission angles and positions, the ultrasonic system identifies the position and angle at which it achieves a match of the posterior and inferior calcaneal contour that resembles that of previous measurements obtained in a healthy reference population most closely. Once the preferred position and angle resulting in the best match have been identified, the ultrasound system measures then SOS and BUA using that particular position and angle and measuring an area 1.5 cm anterior to the posterior cortex and 1.5 cm superior to the inferior cortex.

Scans are repeated one day later: Initially, patients are scanned using the first ultrasonic prototype system that is not capable of B-scan imaging and transmission of ultrasonic signals at multiple transmission angles.

Patients are then re-scanned on the second ultrasonic prototype system. The second ultrasonic system acquires multiple B-scan images at multiple different positions over the calcaneus using multiple different transmission angles at each position. The ultrasonic system identifies the posterior contour and the inferior contour of the calcaneus on the B-scan images. As the transmission angle changes, the contour formed by the posterior and inferior cortex of the calcaneus changes. The ultrasound system performs a matching procedure between the calcaneal contour measured on the initial scan one day earlier and the calcaneal contour measured on the second scan. Once the position and the transmission angle have been identified that yield the closest match to the previous measurement in the same patient, SOS and BUA are re-measured.

The results demonstrate the in vivo reproducibility of SOS and BUA measurements improve markedly when using the second ultrasound system that allows contour matching of the calcaneus and signal transmission and reception at multiple transmission angles.

Example 4

Improvement in Image Quality and Anatomic Accuracy of Three-Dimensional Displays of Ultrasonic Data Using Computer Controlled Two-Dimensional Ultrasonic Image Acquisition at Multiple Transmission Angles A patient with a renal cell carcinoma involving the inferior pole of the left kidney is subjected to ultrasound scanning. Initially, the patient is scanned using a standard clinical ultrasound system (Acuson Sequoia™, Acuson, Mountainview, Calif. ) with a 3.5 MHz transducer. A physician trained in diagnostic ultrasound holds the transducer in his hand. The physician positions the ultrasound transducer over the area of the tumor. The physician directs the transducer so that the tumor is imaged in superoinferior orientation in the sagittal plane. The ultrasound system provides real time images of the tumor. The depth of interrogation is adjusted to include all tumor boundaries. The physicians then rotates the transducer with a sweeping motion of his hand and wrist from medial to lateral while maintaining the same skin contact area and while continuing to scan. In this fashion, multiple images covering the mediolateral extent of the tumor are acquired. The images are stored digitally and transferred to an independent computer image analysis, reconstruction, and viewing station. The computer station is used to generate three-dimensional reconstructions of the tumor using echogenicity based thresholding techniques with subsequent surface or volume reconstruction techniques. The three-dimensional reconstruction of the tumor is then used to quantify the tumor volume using previously established techniques (see also Heuck et al., J Comp. Assist. Tomogr. Vol. 13, No. 2, pp. 287–293, 1989).

The patient is then re-scanned using a prototype ultrasound system that provides for acquisition of ultrasound images at multiple transmission angles using a computer controlled multiple transmission angle positioner. Images are also acquired in real time mode with an ultrasonic transmission frequency of 3.5 MHz. The physician directs the ultrasound transducer unit over the area of the tumor where it is held in place by a computer controlled positioner. The transducer unit is oriented so that the tumor is imaged in superoinferior orientation in the sagittal plane. The depth of interrogation is adjusted to include all tumor boundaries. Once the transducer has been adequately positioned over the tumor, the computer unit instructs the transducer to acquire multiple images at multiple transmission angles through the tumor. Since each transmission angle is computer defined, the exact anatomic/spatial orientation of each image relative to the transducer is known and stored along with the two-dimensional image data. The data are stored digitally and transferred to an independent computer image analysis, reconstruction, and viewing station. The computer station is used to generate three-dimensional reconstructions of the tumor using echogenicity based thresholding techniques with subsequent surface or volume reconstruction techniques. The three-dimensional reconstruction of the tumor is then used to quantify the tumor volume using previously established techniques (see also Heuck et al., J Comp. Assist. Tomogr. Vol. 13, No. 2, pp. 287–293, 1989).

Finally, the patient is re-scanned using a contrast-enhanced spiral CT scan through the abdomen. The contrast-enhanced spiral CT images highlight the tumor very clearly agains surrounding, less enhancing tissues. CT images are also transferred to an independent computer workstation equipped with software for three-dimensional image reconstruction using thresholding techniques with subsequent surface or volume reconstruction. The resultant three-dimensional reconstructions are also used to quantify the volume of the tumor based on the CT data.

The results show that three-dimensional displays of ultrasound images obtained using a computer controlled multiple transmission angle positioner demonstrate less image artifacts and correlate better with the 3D CT reconstruction than three-dimensional displays of ultrasound images obtained using the hand-held sweeping technique. The results show also that the 3D tumor volume quantified based on three-dimensional displays of ultrasound images obtained using a computer controlled multiple transmission angle positioner correlates better with the tumor volume quantified based on the 3D CT reconstruction than the 3D tumor volume obtained based on three-dimensional displays of ultrasound images obtained using the hand-held sweeping technique.

PUBLICATIONS
U.S. PATENT DOCUMENTS

| | | |
|---|---|---|
| 3,648,685 | Mar. 14, 1972 | Hepp, J. A., et al. |
| 3,713,329 | Jan. 30, 1973 | Munger, D. W. |
| 3,782,177 | Jan. 1, 1974 | Hoop, J. M. |
| 3,847,141 | Nov. 12, 1974 | Hoop, J. M. |
| 4,043,181 | Aug. 23, 1977 | Nigam, A. K. |
| 4,048,986 | Sep. 20, 1977 | Ott, J. H. |
| 4,056,970 | Nov. 8, 1977 | Sollish, B. D. |
| 4,224,829 | Sep. 30, 1980 | Kawabuchi, M., et al. |
| 4,235,243 | Nov. 25, 1980 | Saha, S. |
| 4,242,911 | Jan. 6, 1981 | Martin, H. E. |
| 4,361,154 | Nov. 30, 1982 | Pratt, G. W. |
| 4,421,119 | Dec. 20, 1983 | Pratt, G. W. |
| 4,446,737 | May 8, 1984 | Hottier, F. |
| 4,522,068 | Jun. 11, 1985 | Smith, G. E. |
| 4,530,360 | Jul. 23, 1985 | Duarte, L. R. |
| 4,658,827 | Dec. 21, 1987 | He, P., et al. |
| 4,688,428 | Aug. 25, 1987 | Nicolas, J. -M. |
| 4,702,258 | Oct. 27, 1987 | Nicolas, J. -M., et al. |
| 4,774,959 | Oct. 4, 1988 | Palmer, S. B., et al. |
| 4,830,015 | May 16, 1989 | Okazaki, K. |
| 4,913,157 | Apr. 3, 1990 | Pratt, G. W., et al. |
| 4,930,511 | Jun. 5, 1990 | Rossman, P. J., et al. |
| 5,042,489 | Aug. 27, 1991 | Wiener, S. A., et al. |
| 5,054,490 | Oct. 8, 1991 | Rossman, P. J., et al. |
| 5,099,849 | Mar. 31, 1992 | Rossman, P. J., et al. |
| 5,119,820 | Jun. 9, 1992 | Rossman, P. J., et al. |
| 5,218,963 | Jun. 15, 1993 | Mazess, R. B. |
| 5,271,403 | Dec. 21, 1993 | Paulos, J. J. |
| 5,343,863 | Sep. 6, 1994 | Wiener, S. A., et al. |
| 5,349,959 | Sep. 27, 1994 | Wiener, S. A., et al. |
| 5,452,722 | Sep. 26, 1995 | Langton, C. M. |
| 5,483,965 | Jan. 16, 1996 | Wiener, S. A., et al. |
| 5,603,325 | Feb. 18, 1997 | Mazess, R. B., et al. |
| 5,649,538 | Jul. 22, 1997 | Langton, C. M. |

FOREIGN PATENT DOCUMENTS
WO 80/02796 June 9, 1980 Pratt, G.
OTHER PUBLICATIONS

Agren, M., et al., Calc Tiss Int, vol. 48, pp. 240–244, 1991.
Bates, B., et al., in: "A guide to physical examination and history taking, 6th edition", Bates, B., et al., eds., pp. 427–447, 1995.
Biot, M. A., J Acoust Soc Am, vol. 34, pp. 1254–1264, 1962.
Bradenburger, G., et al., J Bone Miner Res, vol. suppl. 1, pp. S184, 1992.
Dretakis, E., et al., Br J Radiol, vol. 67, pp. 636–638, 1994.
Faulkner, K. G., et al., Am J Roentgenol, vol. 157, pp. 1229–37, 1991.
Gluer, C. C., et al., J Bone Min Res, vol. 7 (9), pp. 1071–1079, 1992.
Gluer, C. C., et al., Calc Tiss Int, vol. 55, pp. 46–52, 1994.

-continued
PUBLICATIONS
U.S. PATENT DOCUMENTS

Goss, S. A., et al., J Acoust Soc Am, vol. 64 (2), pp. 423–457, 1978.
Greespan, M., et al., J Acoust Soc Am, vol. 31, pp. 75–76, 1959.
Hans, D., et al., Bone, vol. 16, pp. 476–480, 1995.
Heuck, A. et al., J Comp. Assist. Tomogr. Vol. 13, No. 2, pp. 287–293, 1989
Lang, P., et al., Radiol Clin North Am, vol. 29, pp. 49–76, 1991.
Langton, C. M., et al., Bone, vol. 18, 6, pp. 495–503, 1996.
Langton, C. M., et al., Eng Med, vol. 13, pp. 89–91, 1984.
McCloskey, E. V., et al., Clin Sci, vol. 78, pp. 221–227, 1990.
Njeh, C. F., et al., Med Eng Phys, vol. 18, pp. 373–381, 1996.
Rossman, P. J., et al., Clin Phys Physiol Meas, vol. 10, pp. 353–360, 1989.
Schott, A. M., et al., Osteoporosis Int, vol. 3, pp. 249–254, 1993.
Turner, C. H., et al., Calc Tiss Int, vol. 49, pp. 116–119, 1991.
Williams, J. L., J Acoust Soc Am, vol. 91, pp. 1106–1112, 1992.
Williams, P., et al. "Gray's anatomy, 36th British Edition", 1980.
Zagzebski, J. A., et al., Calc Tiss Int, vol. 49, pp. 107–111, 1991.

All documents and publications, including patents and patent application documents, are herein incorporated by reference to the same extent as if each publication were individually incorporated by reference.

We claim:

1. An ultrasonic system for multiple transmission angle ultrasonic interrogation in tissues with heterogenous structures that alter ultrasonic properties, comprising:

a) a first ultrasonic transducer with an axis of transmission in common with a second ultrasonic transducer, said axis of transmission is through a portion of a tissue, b) an x, y positioner that engages said first ultrasonic transducer and said second ultrasonic transducer, said x, y positioner controllably 1) positions said first ultrasonic transducer and said second ultrasonic transducer in a desired manner between at least a first and a second position while generally maintaining said axis of transmission and 2) establishes predetermined transmission angles for said first ultrasonic transducer and said second ultrasonic transducer to interrogate said portion at multiple transmission angles through heterogenous structures in said portion, c) a z positioner that positions at least one of said first or second ultrasonic transducers, and said z positioner changes the distance of transmission along said axis of transmission between said first ultrasonic transducer and said second ultrasonic transducer, and d) a computational unit designed to manage ultrasonic signal transmission and reception of said first ultrasonic transducer and said second ultrasonic transducer with either BUA or SOS or both and is designed to control movement of said x, y positioner;

wherein said ultrasonic measurements with multiple transmission angles are improved compared to the absence of multiple transmission angles.

2. The ultrasonic system of claim 1, further comprising a z positioner that positions at least one of said first or second ultrasonic transducers, and said z positioner changes the distance of transmission along said axis of transmission between said first ultrasonic transducer and said second ultrasonic transducer.

3. The ultrasonic system of claim 2, wherein said computational unit is designed to remove or filter interference or scatter detected at multiple transmission angles.

4. The ultrasonic system of claim 3, wherein said x, y positioner can establish at least three predetermined transmission angles.

5. The ultrasonic system of claim 4, wherein said transmission angles vary overall by at least thirty degrees.

6. The ultrasonic system of claim 1, wherein said first transducer and said second transducer can transmit and receive signals to change the direction of transmission between said first transducer and said second transducer to reduce ultrasonic artifacts due to variations in tissue interposed along the transmission path.

7. The ultrasonic system of claim 6, wherein said x, y positioner comprises a frame to maintain said axis of transmission between said first and second ultrasonic transducers, said frame engages an x track and said x track engages a y track, thereby an operator can move said first and second ultrasonic transducers manually in either an x or y dimension or combination thereof with respect to an anatomical region.

8. The ultrasonic system of claim 7, wherein said x, y positioner can accommodate an appendage and said appendage is held in a predetermined position in said ultrasonic system relative to said x, y positioner.

9. The ultrasonic system of claim 1, wherein said x, y positioner is automatically controlled by said computational unit.

10. The ultrasonic system of claim 9, wherein said computational unit comprises a computational program to calculate BUS or SOS or both at multiple transmission angles.

11. The ultrasonic system of claim 10, wherein said computational unit is designed to instruct said x, y positioner to position said first ultrasonic transducer and said second ultrasonic transducer to interrogate said tissue with respect to an anatomic landmark and said x, y positioner generally maintains said axis of transmission between said first ultrasonic transducer and said second ultrasonic transducer at a preselected set of coordinates in relation to said anatomic landmark.

12. The ultrasonic system of claim 11, wherein said anatomic landmark is part of an anatomical region selected from the group consisting of a knee, an ankle, and tibia, and further wherein said x, y positioner is adapted to accommodate said anatomical region and said first ultrasonic transducer and said second ultrasonic transducer are adapted for interrogation using broadband ultrasonic attenuation of dense tissue comprising bone.

13. The ultrasonic system of claim 10, wherein said computational unit is designed to remove or filter interference or scatter detected at multiple transmission angles.

14. The ultrasonic system of claim 1, wherein said computational unit can 1) average signals from multiple transmission angles and 2) instruct said x, y positioner to a position over said anatomic landmark, thereby said first ultrasonic transducer and second ultrasonic transducer have an axis of transmission generally through said anatomic landmark.

15. An ultrasonic system for tissue ultrasonic interrogation for broadband ultrasonic attenuation, comprising:
  a) a first ultrasonic transducer with an axis of transmission through an anatomical region to be interrogated,
  b) a second ultrasonic transducer with said axis of transmission through said anatomical region to be interrogated, wherein ultrasonic monitoring between said first ultrasonic transducer and said second ultrasonic transducer is permitted,
  c) a positioning unit to vary the transmission angle of the axis of transmission with respect to said,
  d) a computational unit designed to manage ultrasonic signal transmission of said first ultrasonic transducer, to manage ultrasonic signal reception of said second ultrasonic transducer and to control the transmission angle of the axis of transmission; and
  e) said first transducer and said second transducer can transmit and receive signals to change the direction of transmission between said first transducer and said second transducer to reduce ultrasonic artifacts due to variations in tissue interposed along the transmission path.

16. The ultrasonic system of claim 15, wherein said positioning unit comprises an x,y positioner for said first ultrasonic transducer and said second ultrasonic transducer at can establish at least 3 predetermined transmission angles.

17. The ultrasonic system of claim 16, wherein said computational unit comprises a program to generate an anatomic landmark at multiple transmission angles and said positioning unit comprises a z positioner controlled by said computational unit.

18. The ultrasonic system of claim 15, wherein said x,y positioner is designed to position said first ultrasonic transducer and said second ultrasonic transducer, wherein said first axis of transmission at each transmission angle generally passes through the same anatomical region that is no more than about 5 to 8 cm squared.

19. A computer program product on a computer readable medium, comprising:
  a) instructions for a x, y positioning unit to vary the transmission angle of a transducer or plurality of transducers at a plurality of transmission angles in an anatomical region with respect to an anatomic landmark,
  b) instructions for interrogating said anatomical region at a preselected set of coordinates in relation to said anatomic landmark with said transducer or said plurality of transducers at said plurality of transmission angles, and
  c) instructions for recording at least one ultrasonic property at said plurality of transmission angles,
  wherein instructions (a) through (c) facilitates a clinically relevant measurement and instructions (a) through (c) are stored on a computer retrievable medium.

20. The computer program product of claim 19, further comprises: instructions for comparing ultrasonic signals at a plurality of transmission angles and said clinical measurement is dense tissue BUA or dense tissue SOS.

* * * * *